(12) United States Patent
Sterman Heimann

(10) Patent No.: US 9,796,760 B2
(45) Date of Patent: Oct. 24, 2017

(54) MODIFIED PEPTIDE, CB RECEPTOR LIGAND, KIT IN VITRO PROCESS FOR EVALUATING CB RECEPTOR BONDS, USES, PHARMACEUTICAL COMPOSITION FOR MODULATING CB RECEPTOR ACTIVITY

(71) Applicant: Proteimax Biotecnologia Ltda, Sao Paulo (BR)

(72) Inventor: Andrea Sterman Heimann, Sao Paulo (BR)

(73) Assignee: Proteimax Biotecnologia Ltda, Butanta (BR)

( * ) Notice: Subject to any disclaimer, the term of this patent is extended or adjusted under 35 U.S.C. 154(b) by 0 days.

(21) Appl. No.: 14/412,781

(22) PCT Filed: Jul. 12, 2013

(86) PCT No.: PCT/BR2013/000251
§ 371 (c)(1),
(2) Date: Jan. 5, 2015

(87) PCT Pub. No.: WO2014/008567
PCT Pub. Date: Jan. 16, 2014

(65) Prior Publication Data
US 2015/0291662 A1    Oct. 15, 2015

(30) Foreign Application Priority Data

Jul. 13, 2012 (BR) .......................... 1020120174219

(51) Int. Cl.
| | |
|---|---|
| A61K 38/00 | (2006.01) |
| C07K 7/64 | (2006.01) |
| C07K 7/06 | (2006.01) |
| C07K 7/08 | (2006.01) |
| G01N 33/68 | (2006.01) |
| G01N 33/94 | (2006.01) |

(52) U.S. Cl.
CPC .................. *C07K 7/64* (2013.01); *C07K 7/06* (2013.01); *C07K 7/08* (2013.01); *G01N 33/6872* (2013.01); *G01N 33/948* (2013.01); *A61K 38/00* (2013.01); *G01N 2333/70571* (2013.01)

(58) Field of Classification Search
None
See application file for complete search history.

(56) References Cited

U.S. PATENT DOCUMENTS

| | | | |
|---|---|---|---|
| 2003/0138810 A1* | 7/2003 | Farnet | C07K 14/36 435/6.15 |
| 2003/0198981 A1* | 10/2003 | Farnet | C12N 15/52 435/6.11 |

FOREIGN PATENT DOCUMENTS

WO    2011011847 A2    2/2011

OTHER PUBLICATIONS

Farmanesh, S., et al "High-throughput platform for design and screening of peptides as inhibitors of calcium oxalate monohydrate crystallization," Journal of Crystal Growth (2013), 373, 13-19.*
WIPO International Search Report (on parent international application), dated Oct. 18, 2013.
Riola, V. et al., Novel natural peptide substrates for endopeptidase 24.15, neurolysin, and angiotensis-converting enzyme, J. Biol. Chem. 278(10): 8547-55, 2003.
Fioravanti, Carlos, et al., Voos de fenix: Fragmento de proteina ligado ao controle da pressao arterial pode ajudar a emagrecer e a tratar dependencia quimica, Presquisa FAPESP, p. 44-47, 2008.
Gomes, I. et al., Novel endogenous peptide agonists of cannabinoid receptors, The FASEB Journal, 23(9): 3020-3029, 2009.

* cited by examiner

*Primary Examiner* — Thomas S Heard
(74) *Attorney, Agent, or Firm* — Laurence P. Colton; Smith Tempel Blaha LLC

(57) ABSTRACT

The present invention discloses novel non-natural and modified peptides acting as cannabinoid (CB) receptors ligands, especially CB1 and/or CB2, useful as modulators of its activity; they are also described as a kit and a process in vitro for evaluating the binding to CB receptors, uses and pharmaceutical composition for modulating the CB receptors activity. The invention covers the non-natural peptide of SeqID:1 and those having at least 70% similarity related to the same, including as achievements specialty useful of the invention the non-natural peptides of SeqID:2, SeqID:3, SeqID:4, SeqID:5, SeqID:6.

35 Claims, 19 Drawing Sheets

*p<0.05 vs Control

*p<0.05 vs Control

*p<0.05 vs Control

*p<0.05 vs Control

*p<0.05 vs Control

\* p600 vs. SALINE, p100, p300 *p<0.05*

SEQUENCE LISTING

```
<160> NUMBER OF SEQ ID NOS: 6

<210> SEQ ID NO 1
<211> LENGTH: 10
<212> TYPE: PRT
<213> ORGANISM: Artificial Sequence
<220> FEATURE:
<223> OTHER INFORMATION: Artificial peptide modulator of cannabinoid
      receptors

<400> SEQUENCE: 1

Asp Ile Ile Ala Asp Asp Glu Pro Leu Thr
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Artificial peptide modulator of cannabinoid
      receptors

<400> SEQUENCE: 2

Asp Ile Leu Ala Asp Asp Glu Pro Leu Thr
1               5                   10
```

```
<210> SEQ ID NO 3
<211> LENGTH: 10
<212> TYPE: PRT
<213> ORGANISM: Artificial Sequence
<220> FEATURE:
<223> OTHER INFORMATION: Artificial peptide modulator of cannabinoid
      receptors

<400> SEQUENCE: 3

Asp Ile Ile Ala Asp Asp Ala Pro Leu Thr
1               5                   10

<210> SEQ ID NO 4
<211> LENGTH: 7
<212> TYPE: PRT
<213> ORGANISM: Artificial Sequence
<220> FEATURE:
<223> OTHER INFORMATION: Artificial peptide modulator of cannabinoid
      receptors

<400> SEQUENCE: 4

Asp Ile Ile Ala Asp Asp Glu
1               5

<210> SEQ ID NO 5
<211> LENGTH: 10
<212> TYPE: PRT
<213> ORGANISM: Artificial Sequence
<220> FEATURE:
<223> OTHER INFORMATION: Artificial peptide modulator of cannabinoid
      receptors

<400> SEQUENCE: 5

Asp Ile Ile Ala Asp Asp Glu Ala Leu Thr
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Artificial cyclic peptide modulator of
      cannabinoid receptors

<400> SEQUENCE: 6

Asp Ile Ile Ala Asp Asp Glu Pro Leu Thr
1               5                   10
```

MODIFIED PEPTIDE, CB RECEPTOR LIGAND, KIT IN VITRO PROCESS FOR EVALUATING CB RECEPTOR BONDS, USES, PHARMACEUTICAL COMPOSITION FOR MODULATING CB RECEPTOR ACTIVITY

SEQUENCE LISTING

The instant application contains a Sequence Listing which has been submitted in ASCII format via EFS-Web and is hereby incorporated by reference in its entirety. Said ASCII copy is named 60814-001-sequence-listing-041915.txt and is 1,720 bytes in size.

BACKGROUND OF THE INVENTION

Technical Field

The present invention stands in the fields of pharmacy, medicine, chemical and biotechnology. More specifically, the present invention described a novel modified peptide acting as cannabinoid (CB) receptors-ligands, specially CB1 and/or CB2, and/or modulator of its activity; they are also described in one kit and one in vitro process for evaluating the binding to CB receptors, uses and pharmaceutical composition for modulating the CB receptors activity.

Prior Art

The cannabinoid system, comprising the cannabinoid receptors (CB), CB1 and CB2 and their endogenous ligands, acts in the ingestion control of food and in the energy metabolism and it is widely expressed in the brain, including cortex, hippocampus, tonsil, pituitary and hypothalamus. CB receptors, particularly CB1, were already identified in several peripheral organs and tissues, including thyroid gland, adrenal gland, reproductive organs, adipose tissue, liver, muscles and gastrointestinal tract.

Several compounds were already detected in the art having modulation activity of this receptor and, between them, the compound Rimonabant—drug used to reduce loss and waist thinning and that was widely use in the pharmaceutical market. However, this compound was subsequently associated to the occurrence of psychiatric diseases in humans, mainly by crossing the hematoencenphalic layer, being then removed from the worldwide market. The hematoencephalic barrier is a barrier highly selective protecting the brain preventing the input, by the system circulation, from potentially harmful substances to the central nervous system. Thus, there is a need in the art of obtaining novel compounds that may modulate the activity of cannabinoid receptors, preferably of the CB1 and/or CB2 receptor, however without having a passage of the same by the hematoencephalic barrier.

The present invention described a novel non-natural peptide, which shows surprisingly results regarding its activity, more especially regarding its use and/or its modulation activity of cannabinoid receptors. The peptide of the present invention, further, has the advantage of being particularly useful for modulating the CB receptors activity and in the treatment of metabolic disorders as, for example, reduce obesity, having the additional advantage of not crossing the hematoencephalic barrier, as show the researches results performed by the inventors.

The search for records disclosed documents only partially relevant for the present invention. Such documents are described bellow, being these place here only with the object of serving the base to the current state of the art, once anyone anticipated or suggests any one of the objects of the present invention.

The document US 2007/213302 shows interaction compounds with CB1 receptor, consisting of pyrazoles and its pharmaceutically acceptable salts acting as antagonists or inverse agonists of the CB1 receptor. The present invention differs from the said document, among other reasons, by showing a novel non-natural peptide, that does not comprise pyrazoles or its salts, and such results are surprisingly, especially regarding the interaction with cannabinoids receptors, facts not described neither suggested in the said document.

The document WO 2011/011847 discloses the use of the hemopressin to treat obesity in a subject and is further disclosed that hemopressin é a compound binding efficiently to the CB1 receptor and does not cross the hematoencephalic barrier. The present invention differs from this document, among other reasons, by showing a novel non-natural peptide, derived from angiotensin conversion enzyme. However, the peptide of the invention is not similar to hemopressin. In addition, the tests results performed by the inventors showed surprisingly, especially regarding the interaction with cannabinoid receptors, facts not described neither suggested in the said document.

Some studies showed by the present inventors in "*Novel Natural Peptide Substrates for Endopeptidase 24.15 Neurolysin, and Angiotensin-converting Enzyme*" (Vanessa Rioli, Fabio C. Gozzo, Andrea S. Heimann, Alessandra Linardi, José E. Krieger, Claudio S. Shida, Paulo C. Almeida, Stephen Hyslop, Marcos N. Eberlin, Emer S. Ferro; 7 de Março de 2003) demonstrated a efficient technique of "screening" novel peptides, which was used in the present invention to detect a peptide with natural sequence for specific proteins regulation. However, any utility regarding the cannabinoid system was found with this natural peptide. The present invention differs from this document, among other reasons, by showing a novel non-natural peptide, which results showed surprisingly, especially regarding the interaction with cannabinoid receptors, fact not described neither cited in any document of the state of the art.

The present invention provides a novel non-natural peptide, that among other functions and uses is ligand for CB receptors and that does not have the inconvenient derived from the interaction with the hematoencephalic layer—and that further provides several useful technical effects. In special, it is disclosed in the present invention a novel non-natural peptide with sequence SeqID:1 and/or with sequence with similarity of, at least, 70% related to the same. The non-natural peptide of the invention is particularly useful as cannabinoid receptors-ligand and/or as modulator of the CB receptors activity. The non-natural peptide of the invention, despite being in general a ligand in a higher level than those known in the art, does not interact with the hematoencephalic barrier, providing additional advantages in the therapeutic use in mammalians.

It follows from the research literature, there were not found documents anticipating or suggesting teachings of the present invention, such that the solution here proposed, to the inventors eyes, has novelty and inventive activity against the state of the art.

BRIEF SUMMARY OF THE INVENTION

The present invention comes to solve a number of problems know from the state of the art as for example providing: a novel non-natural peptide; one cannabinoid receptors-ligand; one kit and in vitro process for evaluating the binding to receptors of cannabinoid receptors; one molecular entity providing these technical effects without passing through the hematoencephalic barrier; and providing novel therapeutic alternatives for treating metabolic disorders and/or obesity. The present invention additionally discloses, between others, the use of the said non-natural peptide for preparing medicines; and a pharmaceutical composition for modulating the CB receptors activity, thereby being useful in the treatment of metabolic disorders and/or for promoting esthetic weight reduction.

However, it is one of the objects of the present invention one modified non-natural peptide, comprising a sequence with at least 70% similarity to the peptide $AA_1$-Asp-$AA_2$-$AA_2$-Ala-Asp-Asp-$AA_3$-$AA_4$, wherein:

$AA_1$ is a tail having between 0-10 amino acids;
$AA_2$ is a hydrophobic amino acid;
$AA_3$ is a charged amino acid;
$AA_4$ is a tail having between 0-13 amino acids.

In one preferred concretization, the said modified peptide comprises at least 90% similarity regarding the amino acids sequence SeqID:1 (or also referred to as Pep 19).

In one preferred concretization, the amino acid tail $AA_1$ is a functionalized tail. In one preferred embodiment, the said tail is a tail TAT with 10 amino acids.

In one preferred concretization, the hydrophobic amino acid $AA_2$ is selected from the group consisting of: alanine, isoleucine, leucine, phenylalanine, valine, proline, glycine, or combinations thereof.

In one preferred concretization, the charged amino acid $AA_3$ is selected from the group consisting of: arginine, lysine, aspartic acid, glutamic acid, or combinations thereof.

In one preferred concretization, the amino acid tail $AA_4$ has 0 amino acid or the amino acid tail $AA_4$ comprises one sequence having proline, leucine and/or threonine amino acids.

In one particularly preferred concretization, the peptide is selected between: SeqID:1, SeqID:2, SeqID:3, SeqID:4, SeqID:5, SeqID:6 or combinations thereof.

In another preferred concretization, the cyclic peptide is shown in the cyclic form of the amino acids sequences SeqID:1, SeqID:2, SeqID:3, SeqID:4, SeqID:5 and/or SeqID:6.

It is another object of the present invention a CB receptors-ligand, the said ligand consisting of at least one non-natural peptide comprising at least 70% similarity to the peptide $AA_1$-Asp-$AA_2$-$AA_2$-Ala-Asp-Asp-$AA_3$-$AA_4$, wherein:

$AA_1$ is a tail having between 0-10 amino acids;
$AA_2$ is a hydrophobic amino acid;
$AA_3$ is a charged amino acid;
$AA_4$ is a tail having between 0-13 amino acids.

In one preferred concretization, the said ligand is an agonist, antagonist or CB inverse agonist.

In one preferred concretization, the said ligand is an agonist, antagonist or CB1 inverse agonist and/or um agonist, antagonist or CB2 receptor inverse agonist.

In one particularly preferred concretization, the ligand is selected between: SeqID:1, SeqID:2, SeqID:3, SeqID:4, SeqID:5, SeqID:6 or its cyclic forms and/or combinations thereof.

There are also other objects of the present invention: one kit and in vitro process for evaluating the binding to CB receptors. The said process comprises at least one step to contact the biological sample having one CB receptor with at least one non-natural peptide comprising at least 70% similarity to the peptide $AA_1$-Asp-$AA_2$-$AA_2$-Ala-Asp-Asp-$AA_3$-$AA_4$, wherein:

$AA_1$ is a tail having between 0-10 amino acids;
$AA_2$ is a hydrophobic amino acid;
$AA_3$ is a charged amino acid;
$AA_4$ is a tail having between 0-13 amino acids.

In one preferred concretization, the non-natural peptide and/or ligand of the kit or of the invention process is chemically modified, to ease the detection/localization of CB receptor(s). In one preferred concretization, the said chemical modification involves the inclusion, to one peptide/ligand region, of one or more chromospheres and/or radioactive element(s).

In one preferred concretization, the said kit or in vitro process provides the selective binding of CB receptors (CB1 and/or CB2, for example), the expression level quantification of such receptors and/or the intensity quantification of peptide/ligand binding to CB receptors, as well as the receptor biological activity.

The said kit or in vitro process is particularly useful for detecting other CB receptors ligand molecular entities, or even molecular entities affecting the binding, selective or not, of the peptides of the invention to the CB receptors.

Said kit or in vitro process is also particularly useful for subsequent personalization of therapeutic treatments based on pharmaceutical compositions comprising the non-natural peptide of the invention. The kit or invention process are, however, applicable to therapeutic prediction/prognosis of the conditions/metabolic disorders evolution, or even of the success therapeutic potential in the treatment of: metabolic disorders comprising obesity, diabetes, high blood pressure (or disease, related condition and/or associated comorbidities); overweight prevention; appetite regulation; satiety induction; weight gain prevention after successful weight loss; energy consumption increase; esthetic weight reduction; or bulimia.

It is other object of the present invention the use of at least one non-natural peptide comprising at least 70% similarity to the peptide $AA_1$-Asp-$AA_2$-$AA_2$-Ala-Asp-Asp-$AA_3$-$AA_4$, wherein:

$AA_1$ is a tail having between 0-10 amino acids;
$AA_2$ is a hydrophobic amino acid;
$AA_3$ is a charged amino acid;
$AA_4$ is a tail having between 0-13 amino acids, for preparing a medicine for modulating the CB receptors activity, being useful in the treatment of metabolic syndrome and/or to promote the esthetic weight reduction in a mammalian.

In one particularly preferred concretization, the said use is one or more non-natural peptide selected between: SeqID:1, SeqID:2, SeqID:3, SeqID:4, SeqID:5, SeqID:6 or its cyclic forms, and/or combinations thereof.

It is other object of the invention a pharmaceutical composition for modulating the CB receptors activity in a mammalian, the said composition comprising: a pharmaceutically acceptable vehicle; and, as active principle, one or more non-natural peptide comprising at least 70% similarity to the peptide $AA_1$-Asp-$AA_2$-$AA_2$-Ala-Asp-Asp-$AA_3$-$AA_4$, wherein:

$AA_1$ is a tail having between 0-10 amino acids;
$AA_2$ is a hydrophobic amino acid;
$AA_3$ is a charged amino acid;
$AA_4$ is a tail having between 0-13 amino acids.

and/or pharmaceutically acceptable salts of the said peptide(s).

In one preferred embodiment, the said pharmaceutical composition further comprises other active principles. In one preferred embodiment, the pharmaceutical composition is shown in the form of tablet, gel, injectable solution or inhalable forms or in adhesive.

These and other objects of the present patent application will be immediately reclaimed by those skilled in the art and by the companies with interest on the segment, and will be described in detail enough for its reproduction in the following description.

BRIEF DESCRIPTION OF THE DRAWINGS

The following detailed description and the attached figures illustrate the main characteristics and achievements of the present invention, showed in details to provide better technical support to the subject, so that the same may understand and reproduce the inventive concept of the invention in any possible achievements. Such details should not be understood in a limited way and they are intended to only illustrate some of the preferred achievements of the present invention.

DETAILED DESCRIPTION OF PREFERRED EMBODIMENTS

Figure 1:
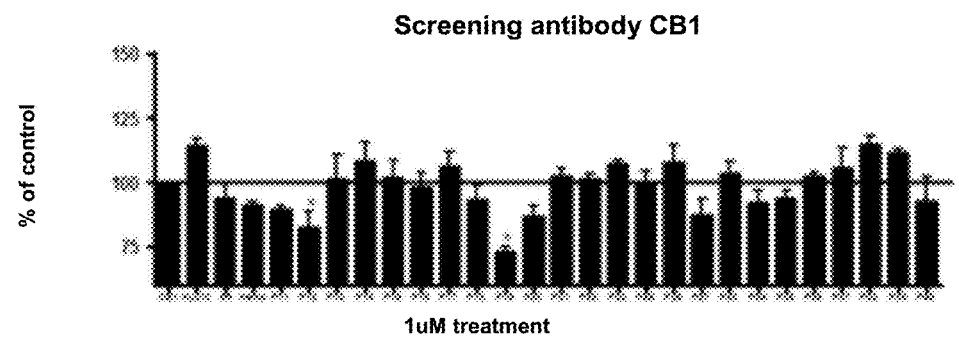
FIG. 1 shows a screening of novel ligands for the CB1 receptor.

The common inventive concept to the several objects of the invention is to provide a non-natural peptide useful as CB receptors-ligand. From this inventive concept, several applications were implemented by the inventors using the said inventive concept, including, among others: the modulation, selective or not, of the activity of such receptors; the achievement of a kit and a in vitro process for evaluating the binding to CB receptors; the use of the said peptide as auxiliary when identifying other CB molecular entities ligands or that interfere in the peptide binding of the invention to CB receptors; the use of the said peptide for preparing pharmaceutical composition for modulating the CB receptors activity.

For the present invention purposes, the following definitions are used:

Modified Peptide

In the context of the present patent application, it should understand "modified peptide" as a non-natural peptide, artificially modified in order to achieve the objectives of the present invention.

At Least 70% Similarity

In the context of the present patent application, it should understand "at least 70% similarity" as the fact of maintaining at least 70% similarity and/or identity with the peptide of (SeqID:1). In the context of the present peptide, this would be the same as to modify up to 3 amino acids such that the peptide maintains the same activity showed along this patent application.

Cyclic or Circular Peptide

In the context of the present patent application, it should understand "cyclic peptide" or "circular" as a peptide that had a covalent binding between both ends of a nucleic acid linear molecule (simple or double tape) involving the union of the 3'-hydroxyl to the 5'-phosphate through any method known in the art, particularly by the ligase enzyme activity. The cyclic peptide may be used replacing the linear peptide due to the fact of being more difficult to be degraded, since its ends or attack zones by hydrolysis enzymes are not so exposed as in a linear peptide.

Ligand to the CB Receptor

In the context of the present patent application, it should understand "ligand to the CB receptor" as a compound or molecule interacting with the CB system and/or CB1 or CB2 receptors in a way to promote any direct or indirect effect of binding to the said receptors.

Agonist

In the context of the present patent application, it should understand "agonist" as a medication, drug, hormone, neurotransmitter or other sign molecule forming a complex with a receptor site, in this way acting an active answer of a cell.

Inverse Agonist/Antagonist

In the context of the present patent application, it should understand "inverse agonist or antagonist" as agent(s) (for example: medications, drugs, hormones or enzymes) that bind to the agonists receptors and produce pharmacological effects opposed to the agonists, in such a way that the action of one inhibits partially or totally the effect of the other. Particularly, a compound will be an inverse agonist when acting in the presence of an agonist, but reducing its activity, an antagonist will be a compound that will block totally the agonist activity.

Modulating the CB Receptor Function

In the context of the present patent application, it should understand "modulating the CB receptor function" as an interaction entailing in the biochemical activity change of the CB receptor, particularly CB1 or CB2. It is understood that the change is positive when occurring an antagonist or inverse agonist effect in the CB receptors and that the change is negative when occurring an agonist effect in the CB receptors.

Pharmaceutical Composition

In the context of the present patent application, it should understand "pharmaceutical composition" as all or any composition having an active principle, with prophylactic, palliative and/or curative purposes, acting in a way of maintaining and/or restoring the homeostasis, and may be administered in a topical, parenteral, enteral and/or intrathecal way.

Pharmaceutically Acceptable Formulation

In the context of the present patent application, it should understand "pharmaceutically acceptable formulation" as a formulation having pharmaceutically acceptable excipients and carriers well known by those skilled in the art, as it is the dosages development and convenient treatments to use in special compositions tat can be described in one number of treatment regiments, including oral, parenteral, intravenous, intranasal, intravitreal and intramuscular, intracerebral, intracerebroventricular and intraocular and its administration and/or formulation.

Metabolic Disorders

In the context of the present patent application, "metabolic disorders" just be understood as any metabolic disorder changing the normal physiological functions of a human being, in special mammalians. In the context of the present patent application, the term comprises chronic and acute diseases that generate physiological changes in the human being, such as: dyslipidemia with several causes, obesity, hypertension, diabetes mellitus, type 1 diabetes, metabolic syndrome, atherosclerosis, among other metabolic disorders.

The present invention discloses, among other objects, a non-natural peptide comprising at least 70% similarity to the peptide $AA_1$-Asp-$AA_2$-$AA_2$-Ala-Asp-Asp-$AA_3$-$AA_4$, wherein:

$AA_1$ is a tail having between 0-10 amino acids;
$AA_2$ is a hydrophobic amino acid;
$AA_3$ is a charged amino acid;
$AA_4$ is a tail having between 0-13 amino acids.

Preferably, the modified non-natural peptide has functionalized amino acid tail $AA_1$.

Preferably, the modified non-natural peptide has the hydrophobic amino acid $AA_2$ selected from the group consisting of: alanine, isoleucine, leucine, phenylalanine, valine, proline, glycine, or combinations thereof.

Preferably, the modified non-natural peptide has charged amino acid $AA_3$ selected from the group consisting of: arginine, lysine, aspartic acid, glutamic acid, or combinations thereof.

Preferably, the modified non-natural peptide has amino acid tail $AA_4$ with 0 amino acid, or amino acid tail $AA_4$ comprising a sequence having proline, leucine and/or threonine amino acids.

Preferably, the modified non-natural peptide has at least 90% similarity regarding the amino acids sequence SeqID:1 (Pep 19).

Preferably, the modified non-natural peptide has to be selected between peptides with sequence: SeqID:1; SeqID:2; SeqID:3; SeqID:4; SeqID:5; SeqID:6; its cyclic forms; or combinations thereof The present invention also provides a kit and in vitro process for evaluating the binding to CB receptors. The said process comprises at least a step of contacting a biological sample having one CB receptor with at least one non-natural peptide of the invention.

Preferably, the non-natural peptide and/or ligand of the kit or of the invention process is chemically modified, to ease the detection/localization of CB receptor(s). In one preferred concretization, the said chemical modification involves the inclusion, to a peptide/ligand region, of one or more chromospheres and/or radioactive element(s).

The said kit or in vitro process provides the selective binding of CB receptors (CB1 and/or CB2, for example), the expression level quantification of such receptors and/or the intensity quantification of peptide/ligand binding to CB receptors. The said kit or in vitro process is particularly useful for detecting other CB receptors ligand molecular entities, or even molecular entities affecting the binding, selective or not, of the peptides of the invention to the CB receptors.

The said kit or in vitro process is also particularly useful for the subsequent customization of therapeutic treatments based on pharmaceutical compositions comprising non-natural peptide of the invention. The kit or invention process are, however, applicable to the therapeutic prediction/prognosis of the conditions/metabolic disorders evolution, or even of the success therapeutic potential in the treatment of: metabolic disorders comprising obesity, diabetes, high blood pressure (or disease, related condition and/or associated comorbidities); overweight prevention; appetite regulation; satiety induction; weight gain prevention after successful weight loss; energy consumption increase; esthetic weight reduction; or bulimia.

The peptide of the invention has several applications, being particularly useful, between other applications, for modulating the CB receptors activity, being useful for metabolic conditions or diseases treatment associated to the cannabinoid (CB) receptors activity modulation—with no undesirable effects known from congeners available in the state of the art. The peptide of the invention is particularly useful as an antagonist or CB1 and/or CB2 inverse agonist, acting in an exceeded way over the congeners available in the art and not crossing the hematoencephalic barrier.

Additionally, as will be demonstrated in the subsequent examples, the peptide of the invention is deliverable orally to a mammalian, i.e., it does not degrades during the oral ingestion. This characteristic is particularly unexpected, since natural enzymes of a subject do not degrade or degrade a little bit the peptide when in the digestive tract and the same acts effectively when administered orally. The present patent application discloses a pharmaceutical composition comprising the peptide of the present patent application. The present pharmaceutical composition comprises a pharmaceutically acceptable vehicle and may further comprise other actives and/or pharmaceutically acceptable salts thereof, the said peptide being the composition active component, which is administered in the form of tablet, gel, injectable solution or other suitable forms of administration for pharmaceutical and medical purposes.

In one preferred embodiment, the peptide of the present patent application acts as CB1 receptor ligand and, more preferably, the said peptide is agonist, antagonist or CB1 inverse agonist.

In one preferred embodiment, the peptide of the present patent application acts as agonist, antagonist or CB2 inverse agonist.

The peptide of the present patent application is also useful for preparing medicines for the treatment of atherosclerosis, hypertension, diabetes, type 2 diabetes, impaired glucose tolerance (ITG), dyslipidemia, coronary heart diseases, gall bladder diseases, gallstones, osteoartite, cancer, sexual dysfunction and risk of premature death. The peptide of the invention is also useful for preparing a medicine for promoting esthetic weight reduction in a subject. By "esthetic weight loss" means the weight loss of a subject that does not have any medical indication for its body mass reduction.

Further, as will be demonstrated in the following examples, the present peptide is deliverable orally to a mammalian, i.e., it does not degrade during the oral ingestion. This characteristic is particularly unexpected, once natural enzymes of a subject do not degrade or degrade a little bit the peptide when in the digestive tract and the same acts efficiently when administered orally.

The examples here showed intends to only exemplify some of the several ways of concretizing the invention, however, without limiting the scope thereof.

Examples of the Preferred Concretization

Example 1

Peptide Asp-Ile-Ile-Ala-Asp-Asp-Glu-Pro-Leu-Thr

In one concretization of the invention, the peptide has the sequence Asp-Ile-Ile-Ala-Asp-Asp-Glu-Pro-Leu-Thr (indicated in the amino acids sequence SeqID:1 or Pep 19 and identified with the GPCR screening method) and provided action as inverse agonist of the CB1 receptor. FIG. 1 demonstrates the said ligand for CB1 receptor through ELISA with striate membranes (5 μg/pool) treated with 1 μM of each drug for 2 hours in ambient temperature and incubated with anti-CB1 antibody (1:500). The receptor activating percentage was calculated regarding the control, non-treated membrane (100%). The results were showed as average+−SEM (n=5). Significant differences are indicated and p<0.05.

Figure 2:
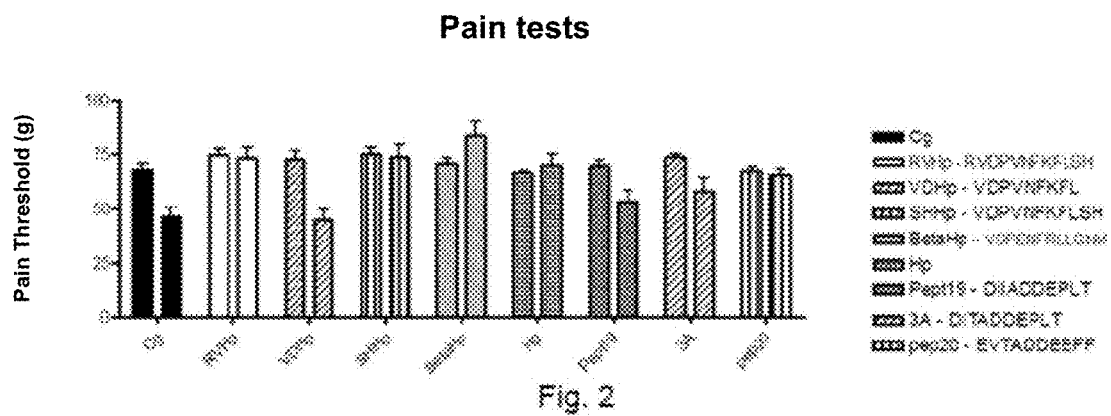
FIG. 2 shows results of pain test after the administration of a preferred concretization of peptide da invention (SeqID:1) in comparison with other peptides known in the art.

Through the effective interaction detection with CB1 receptor were subsequently performed the constant pain tests in the FIG. 2 showing the peptide antihyperalgesic activity of the present invention, hemopressin and other peptides, in vivo. It was performed the comparative analysis of the peptide intraplantar administration over the carrageenan-induced hyperalgesia. Rats were treated with peptide (20 g by leg) immediately before the carrageenan intraplantar administration (200 g by leg) and were evaluated using a pressure apparatus Ugo Basileantes (0 h and empty legs) and 3 h after administration of carrageenan (black legs). Intraplantar-administered rats with vehicle (saline) were subject to the same protocol (control group) and the results were showed as average SEM, n=6-8.

Figure 3:
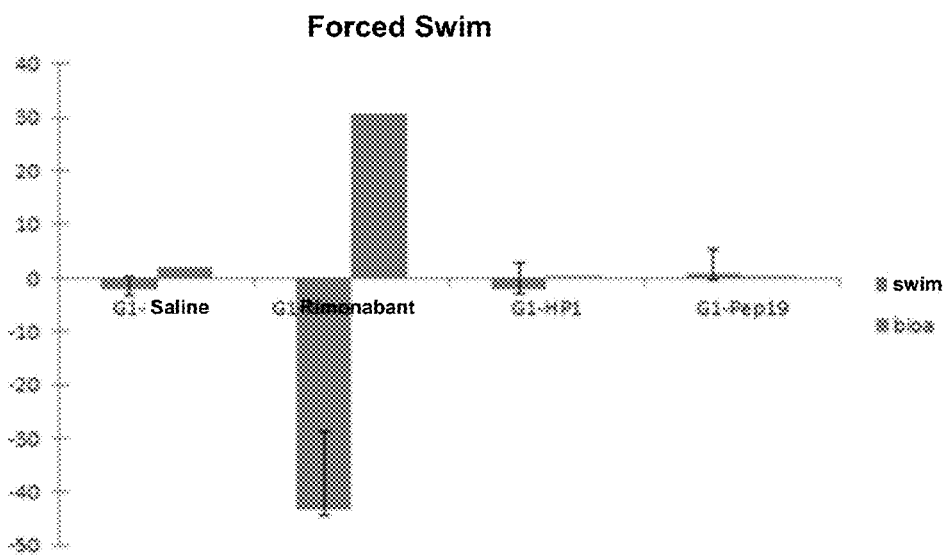
FIG. 3 shows results of depression tests (forced swim) after the administration of a preferred peptide concretization of the present invention (SeqID:1) comparing with other peptides of the art.
Figure 4:
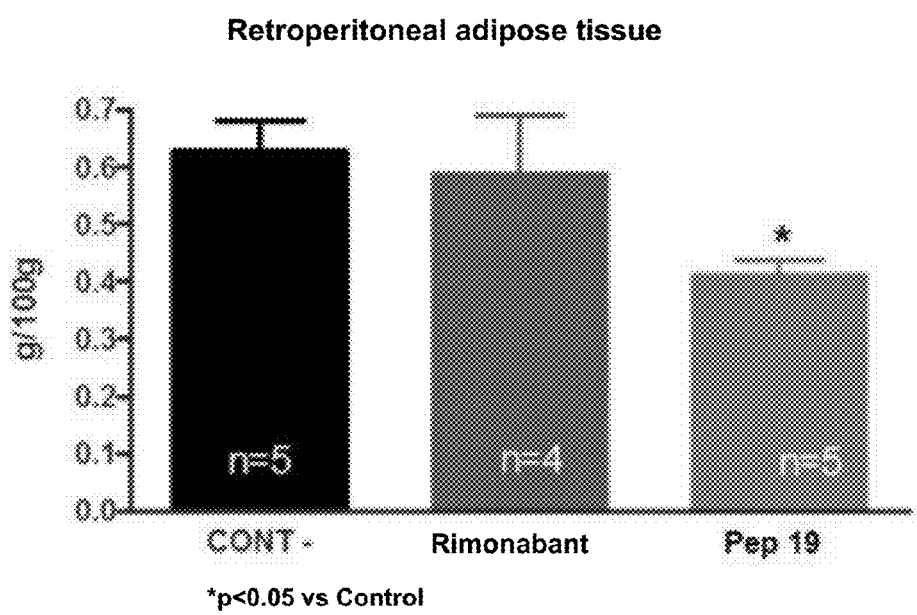
FIG. 4 shows results of retroperitoneal adipose tissue measurement tests after the administration of a preferred peptide concretization of the present invention (SeqID:1).
Figure 5:
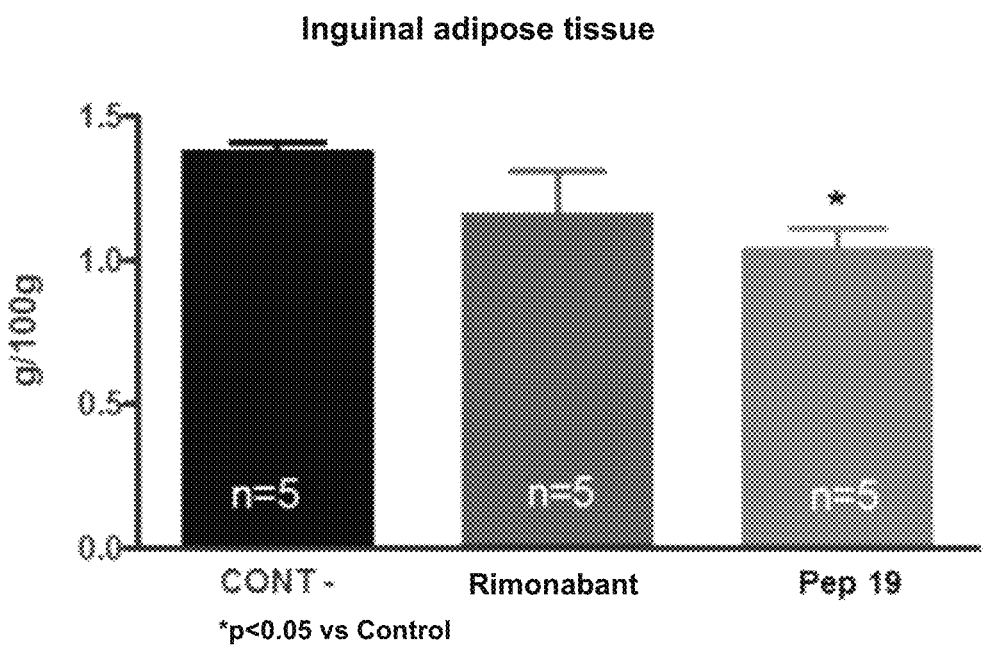
FIG. 5 shows results of inguinal adipose tissue measurement tests after the administration of a preferred peptide concretization of the present invention (SeqID:1).
Figure 6:
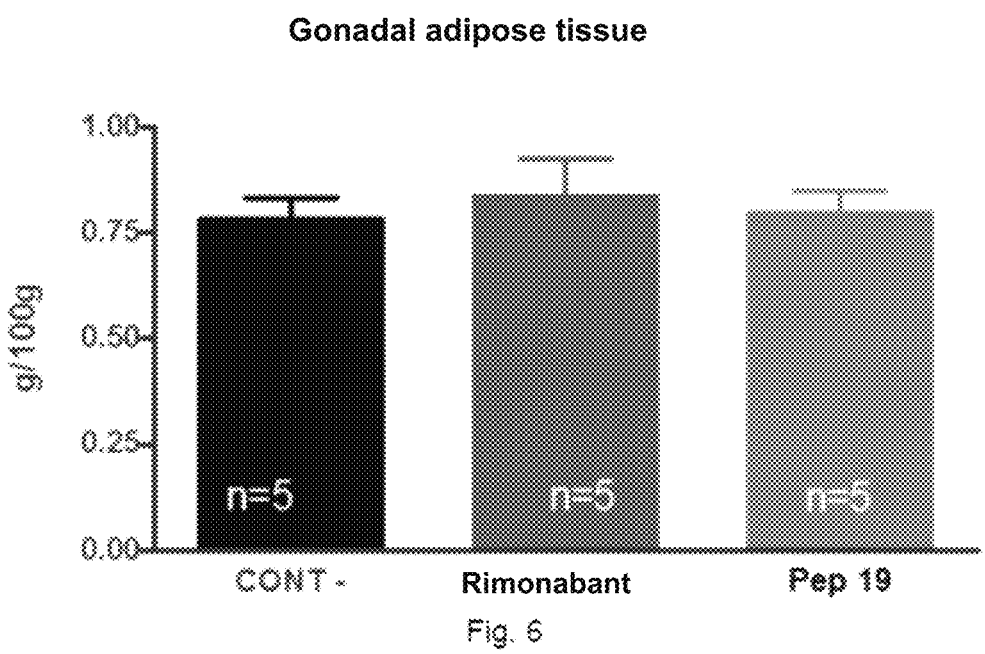
FIG. 6 shows results of gonadal adipose tissue measurement tests after the administration of a preferred peptide concretization of the present invention (SeqID:1).
Figure 7:
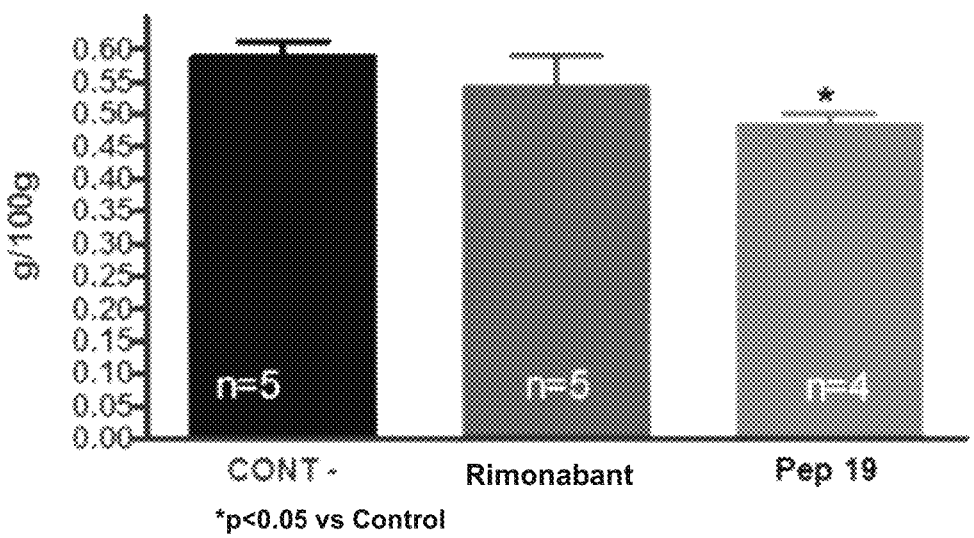
FIG. 7 shows results of mesenteric adipose tissue measurement tests after the administration of a preferred peptide concretization of the present invention (SeqID:1).
Figure 8:
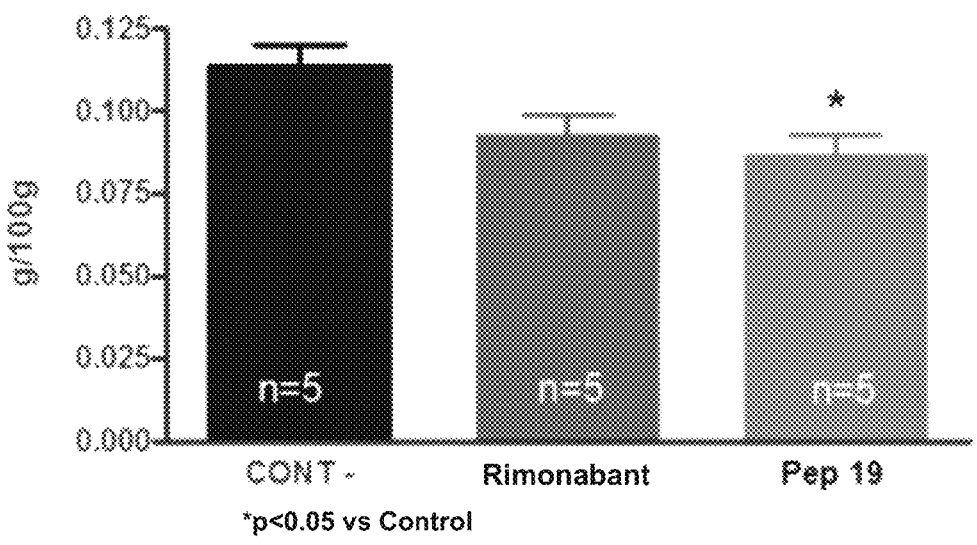
FIG. 8 shows results of brown adipose tissue measurement tests after the administration of a preferred peptide concretization of the present invention (SeqID:1).
Figure 9:
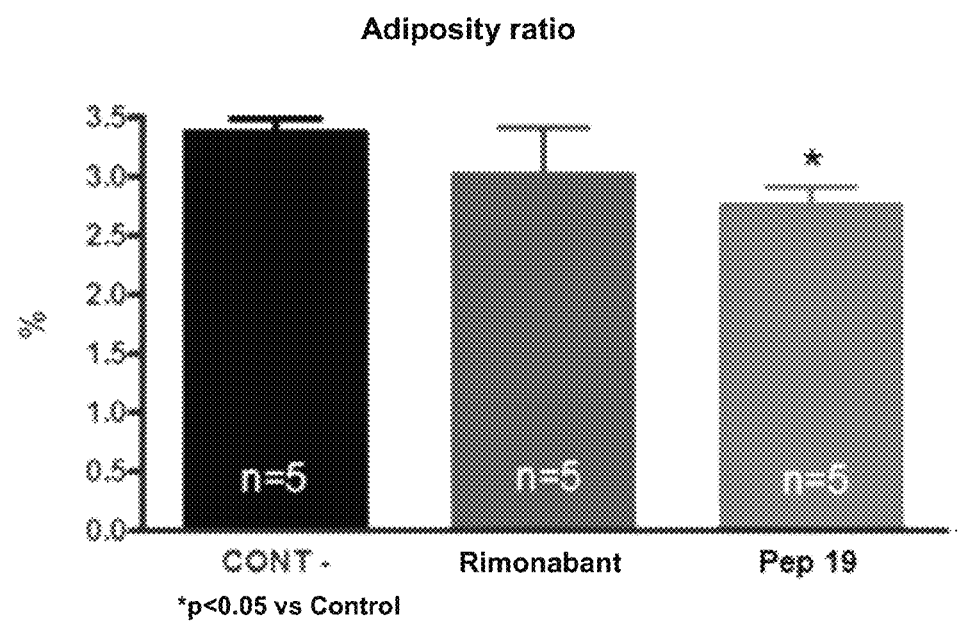
FIG. 9 shows results of the adiposity ratio measurement after the administration of a preferred peptide concretization of the present invention (SeqID:1).

FIG. 3 shows the peptide application effects of the present invention in a depression model (forced swim) and it was found that the peptide, contrary to Rimonabant, does not cause depression. The forced swim test was performed based on the previous tests ([Harkin et al., 2004], [Petit-Demouliere et al., 2005] and [Treit and Menard, 1998]). Rats were placed in a pool with water (24+−1° C.) up to 1 m deep (so the mouse cannot touch the bottom) and 20 cm of the pool the immobility time (when the animal does not move except few movements necessary to float); the procedure was recorded by 3 experiments after 1, 6 and 9 minutes.

Furthermore, in a treatment acute model (3 days of treatment orally in non-obese wistar rats) it was verified the brown adipose tissue activation, the retroperitoneal, inguinal and brown adipose tissues reduction, as well the adiposity ratio (FIGS. 4 to 9), effects not observed with Rimonabant.

Particularly, it may be verified that the present peptide has activity even when administered orally. This fact is difficult to happen in the art and has several advantages in pharmaceutical and medicine trade administration terms.

Example 2

Peptide Asp-Ile-Leu-Ala-Asp-Asp-Glu-Pro-Leu-Thr

Figure 10:
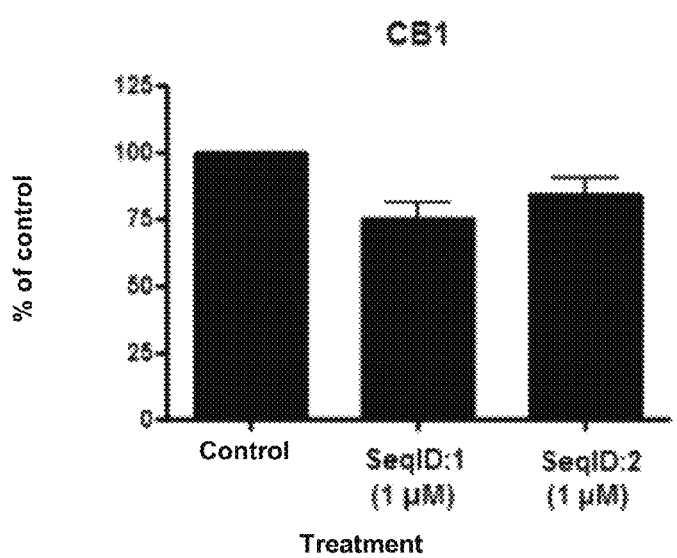
FIG. 10 shows the experimental results in CB1 receptors for another preferred peptide concretization of the present invention (SeqID:2) and comparison to the control and to the SeqID:1.
Figure 11:
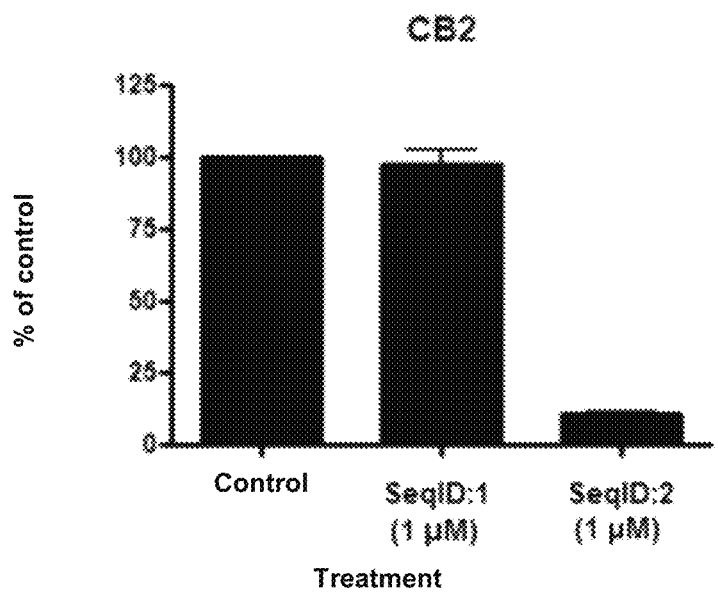
FIG. 11 shows the experimental results in CB2 receptors for another preferred peptide concretization of the present invention (SeqID:2) and comparison to the control and to the SeqID:1.

In one concretization of the invention, the peptide has the sequence Asp-Ile-Leu-Ala-Asp-Asp-Glu-Pro-Leu-Thr (indicated in the amino acids sequence SeqID:2 and identified with the GPCR screening method) and provided action as inverse agonist of the CB2 receptor (FIGS. 10 and 11). FIG. 10 shows the results of the said peptide in comparison with control and the peptide with sequence Seq.ID:1 for CB1 receptor through ELISA with striate membranes (5 μg/pool) treated with 1 μM of each drug for 2 hours in ambient temperature and incubated with anti-CB1 antibody (1:500). The receptor activating percentage was calculated regarding the control, non-treated membrane (100%). The results were showed as average+−SEM (n=5). Significant differences are indicated and p<0.05.

FIG. 11 shows the results of this example peptide in comparison with control and the peptide with sequence Seq.ID:1 for CB2 receptor through ELISA with striate membranes (5 μg/pool) treated with 1 μM of each drug for 2 hours at ambient temperature and incubated with anti-CB1 antibody (1:500). The receptor activating percentage was calculated regarding the control, non-treated membrane (100%). The results were showed as average+−SEM (n=5). Significant differences are indicated and p<0.05.

From these results achieved for example 2, it is concluded that the hydrophobicity change in the third amino acid of the sequence SeqID:1 raises an inverse agonist activity in CB2 receptors. In this way, the presence of a hydrophobic amino acid in this position is important for the activity maintenance in CB1 receptors.

It was also performed an experiment wherein the third amino acid of the SeqID:1 (isoleucine amino acid) was replaced for threonine. However, such replacement caused the biological activity loss expected for the studied peptide. In this way, it is concluded that it is important the presence of hydrophobic amino acid in the third position of the SeqID:1.

Particularly regarding the sequence wherein the third amino acid of the SeqID:1 (isoleucine amino acid) was replaced for threonine, it is interesting to highlight that despite the respective tests have not demonstrated activity detectable against the CB1 or CB2, it may be useful in combinations with other modified peptides indicated above in kits, for evaluating eventual competition by substrate and evaluation of other effects.

Particularly, can be seen that the present peptide has activity even when administered orally. This fact is difficult to happen in the art and has several advantages in pharmaceutical and medicine trade administration terms.

Example 3

Peptide Asp-Ile-Ile-Ala-Asp-Asp-Ala-Pro-Leu-Thr

In one concretization of the invention, the peptide have sequence Asp-Ile-Ile-Ala-Asp-Asp-Ala-Pro-Leu-Thr (indicated in the amino acids sequence SeqID:3 and identified with GPCR screening method) and provided smaller activity in CB1 receptors (FIG. 12) regarding the activity achieved by the amino acids sequence SeqID:1. However, the pharmacological effect was kept.

Figure 12:
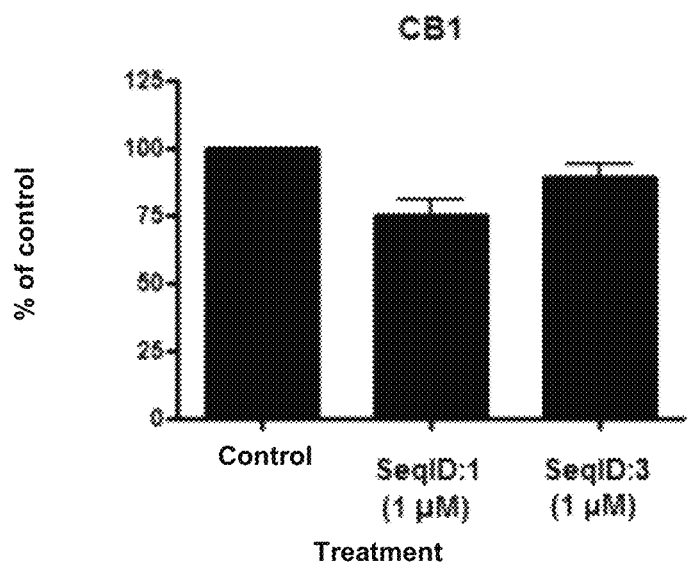
FIG. 12 shows the experimental results in CB1 receptors for another preferred peptide concretization of the present invention (SeqID:3) and comparison to the control and to the SeqID:1.

FIG. 12 shows the results of this example peptide for CB1 receptor through ELISA with striate membranes (5 μg/pool) treated with 1 μM of each drug for 2 hours in ambient temperature and incubated with anti-CB1 antibody (1:500). The receptor activating percentage was calculated regarding the control, non-treated membrane (100%). The results were showed as average+−SEM (n=5). Significant differences are indicated and p<0.05.

In this way, from the results achieved for this example and comparing with the results achieved in the other examples, it is concluded that one charged amino acid in the seventh position (based on the sequence SeqID:1, wherein the seventh amino acid is the glutamic acid) is not essential for the activity in CB1 receptors but it alters this activity.

Particularly, can be seen that the present peptide has activity even when orally administered. This fact is difficult to happen in the art and has several advantages in pharmaceutical and medicine trade administration terms.

Example 4

Peptide Asp-Ile-Ile-Ala-Asp-Asp-Glu

In one concretization of the invention, the peptide has sequence Asp-Ile-Ile-Ala-Asp-Asp-Glu (indicated in the amino acids sequence SeqID:4 and identified with GPCR screening method) and provided improved inverse agonist activity in CB1 receptors, when compared to the activity achieved with the sequence SeqID:1. In this way, the seven amino acids of this sequence are essential for the peptide activity as inverse agonist in CB1.

Figure 13:
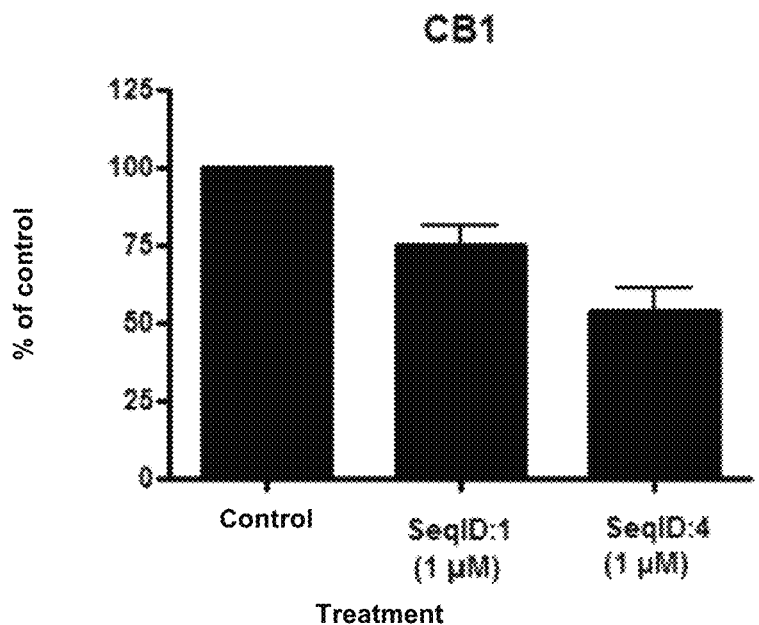
FIG. 13 shows the experimental results in CB1 receptors for another preferred peptide concretization of the present invention (SeqID:4) and comparison to the control and to the SeqID:1.

FIG. 13 shows the results of this example peptide for CB1 receptor through ELISA with striate membranes (5 µg/pool) treated with 1 µM of each drug for 2 hours in ambient temperature and incubated with anti-CB1 antibody (1:500). The receptor activating percentage was calculated regarding the control, non-treated membrane (100%). The results were showed as average+−SEM (n=5). Significant differences are indicated and p<0.05.

Particularly, can be seen that the present peptide has activity even when orally administered. This fact is difficult to happen in the art and has several advantages in pharmaceutical and medicine trade administration terms.

Example 5

Peptide Asp-Ile-Ile-Ala-Asp-Asp-Glu-Ala-Leu-Thr

In one concretization of the invention, the peptide has sequence Asp-Ile-Ile-Ala-Asp-Asp-Glu-Ala-Leu-Thr (indicated in the amino acids sequence SeqID:5 and identified with GPCR screening method) and provided, in low dosages, activity inverse agonist and, in high dosages, showed agonist activity in the endocannabinoid receptors.

However, from this experiment, it is concluded that the eighth amino acid of the original sequence SeqID:1 (Proline) is a peptide agonist component, since the replacement of the proline amino acid (Pro) for the alanine amino acid (Ala) resulted in the improvement of the peptide inverse agonist activity at issue.

It can also be concluded that the conformational fold property removal provided by the proline (Pro) presence in the eighth position of the sequence SeqID:1 raises an agonist activity in endocannabinoid receptors.

Figure 14:
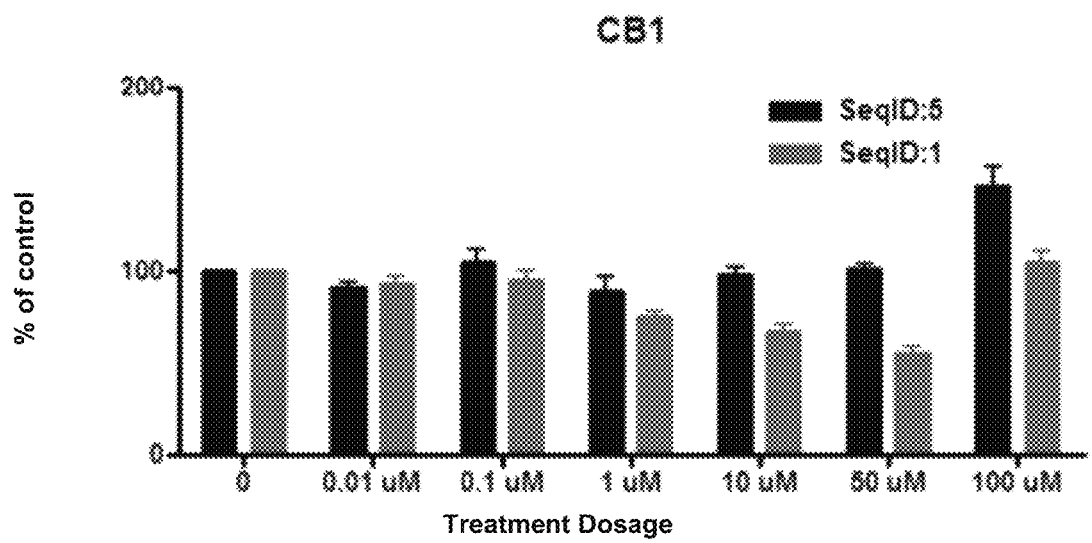
FIG. 14 shows the experimental results in CB1 receptors for another preferred peptide concretization of the present invention (SeqID:5) and comparison to the control and to the SeqID:1.

FIG. 14 shows the results of this example peptide for CB1 receptor through ELISA with striate membranes (5 µg/pool) treated with different dosages of each drug for 2 hours in ambient temperature and incubated with anti-CB1 antibody (1:500). The receptor activating percentage was calculated regarding the control, non-treated membrane (100%). The results were showed as average+−SEM (n=5). Significant differences are indicated and p<0.05.

Particularly, can be seen that the present peptide has activity even when orally administered. This fact is difficult to happen in the art and has several advantages in pharmaceutical and medicine trade administration terms.

Example 6

Cyclic Peptide -Asp-Ile-Ile-Ala-Asp-Asp-Glu-Pro-Leu-Thr-

In one concretization of the invention, the peptide é cyclic, has the sequence Asp-Ile-Ile-Ala-Asp-Asp-Glu-Pro-Leu-Thr (indicated in the amino acids sequence SeqID:1, however cyclic and identified with the GPCR screening method) and provided similar biological activity when comparing to the same non-cyclic peptide. However, the cyclization is interesting mainly in what relates to the peptide half-life time increase in the organism (in vivo). It was also seen that the present peptide has activity even when orally administered. This fact is difficult to happen in the art and has several advantages in pharmaceutical and medicine trade administration terms.

The table 1 summarizes the results data performed with the peptide of the invention in several of its preferred achievements, in wide contrast with the results of natural peptide use known in the previous art.

TABLE 1

| ID | Sequence | Result | Conclusion |
|---|---|---|---|
| Modified peptide 1 (Seq ID 1) | DIIADDEPLT | Effective activity regarding the CB1 | — |
| Modified peptide 2 (Seq ID 2) | DI<u>L</u>ADDEPLT | Reduces the activity regarding the CB1 but raises a strong inverse agonist activity in CB2 | Changing the hydrophobicity in the position 3 (replacing Ile for Leu) raises an activity in CB2. |
| Modified peptide 3 (Seq ID 3) | DIIADD<u>A</u>PLT | Reduces the activity regarding the CB1 (comparatively the SeqID: 1). | To have a charged amino acid in the position 7 is important but it is not essential for CB1 activity, as in the case of hydrophobic amino acid in the position 3. |
| Modified peptide 4 (Seq ID 4) | DIIADDE | Increases the activity regarding the CB1 | The last 3 amino acids are not essential for peptide activity as CB1 inverse agonist, and this minimum sequence would be economically more feasible depending on its effects preservation in vivo. |

TABLE 1-continued

| ID | Sequence | Result | Conclusion |
|---|---|---|---|
| Modified peptide 5 (Seq ID 5) | DIIADDEALT | In low dosages the inverse agonist activity was not detected; and in high dosages became agonist. | The position 8 is a peptide agonist component, once without it improved the inverse agonist activity. Removing the conformational fold property provided by the presence of Pro in the position 9, raises an agonist activity. |
| Modified peptide 6 (Seq ID 6) | DIIADDEPLT (cyclic) | Change in the activity was not detected | In vitro was not detected the difference but may be a big difference in vivo, by changing in the peptide half-life time. |

The in vitro tests reported support the corresponding claimed uses. Further, several and detailed in vivo tests were performed, to support the therapeutic applicability, as summarized below.

Example 7

Test in Retroperitoneal Adipose Tissue

Figure 15:
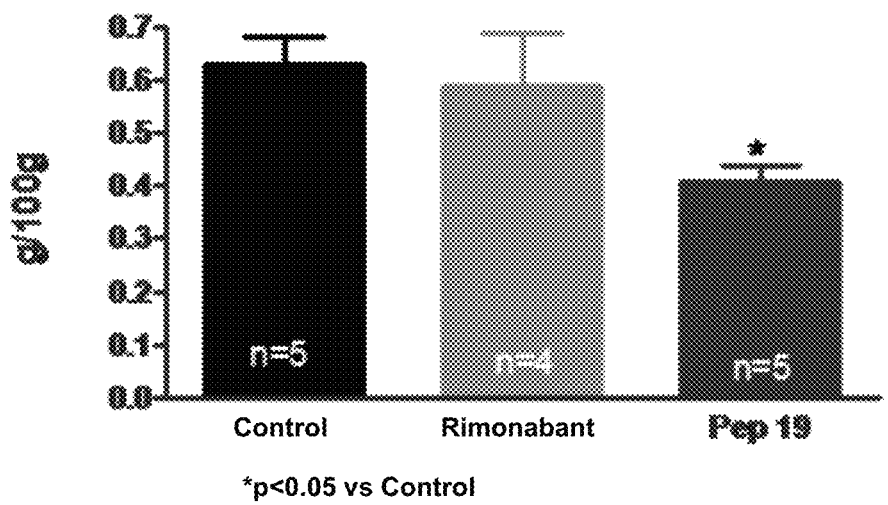
FIG. 15 shows the experimental results in retroperitoneal adipose tissue for a preferred peptide concretization of the present invention (SeqID:1) and comparison to the control and to the Rimonabant.

FIG. 15 shows the application effects of a preferred peptide concretization of the present invention (SeqID:1 or Pep 19) in a retroperitoneal adipose tissue model where Thin wistar rats were treated with a Rimonabant dosage (100 ug/Kg) or peptide 19 (Pep 19 100 ug/Kg) during 3 days orally. The measure of the adipose tissue was performed after finishing the treatment. The results are expressed by the retroperitoneal adipose tissue weight measured for treatment purpose (scale of g/100 g). Rats administered with vehicle (saline) were subject to the same protocol (control). Results are showed as average and average standard deviation SEM, n=4-5.

The results indicate that the retroperitoneal adipose tissue mass was smaller in the animals that received Pep 19 in comparison with the groups that received Rimonabant and/or saline.

Example 8

Test in Gonadal Adipose Tissue

Figure 16:
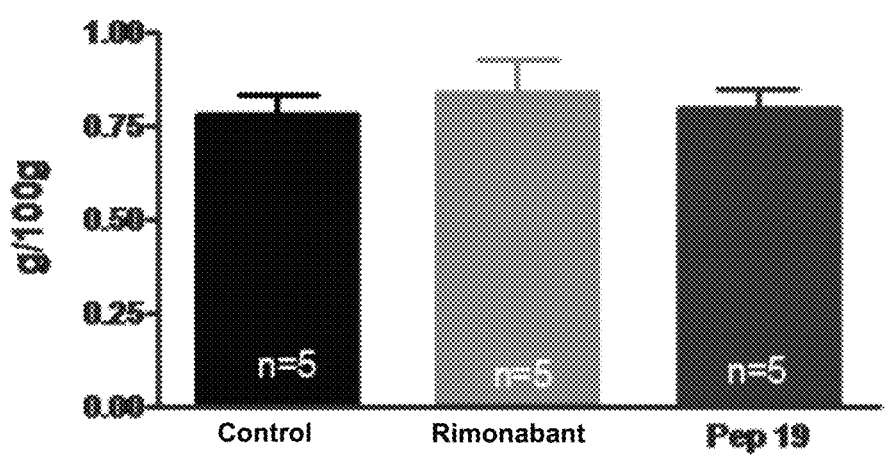
FIG. 16 shows the experimental results in gonadal adipose tissue for a preferred peptide concretization of the present invention (SeqID:1) and comparison to the control and to the Rimonabant.

FIG. 16 shows the application effects of a preferred peptide concretization of the present invention (SeqID:1 or Pep 19) in a gonadal adipose tissue model where Thin wistar rats were treated with a Rimonabant dosage (100 ug/Kg) or peptide 19 (Pep 19 100 ug/Kg) during 3 days orally. The measure of the adipose tissue was performed after finishing the treatment. The results are expressed by the gonadal adipose tissue weight measured at the treatment end (scale of g/100 g). Rats administered with vehicle (saline) were subject to the same protocol (control). Results are showed as average and average standard deviation SEM, n=5.

The results indicate that there is no difference in the gonadal adipose tissue mass between animals that received Pep 19 in comparison with the groups that received Rimonabant and/or saline.

Example 9

Test in Inguinal Adipose Tissue

Figure 17:
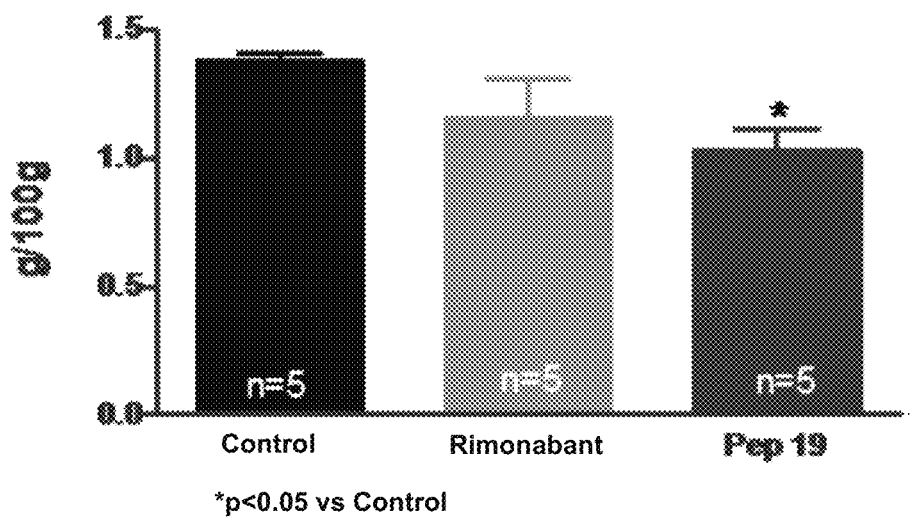
FIG. 17 shows the experimental results in inguinal adipose tissue for a preferred peptide concretization of the present invention (SeqID:1) and comparison to the control and to the Rimonabant.

FIG. 17 shows the application effects of a preferred peptide concretization of the present invention (SeqID:1 or Pep 19) in an inguinal adipose tissue model where Thin wistar rats were treated with a Rimonabant dosage (100 ug/Kg) or peptide 19 (Pep 19 100 ug/Kg) during 3 days orally. The measure of the adipose tissue was performed after finishing the treatment. The results are expressed by the inguinal adipose tissue weight measured at the treatment end (scale of g/100 g). Rats administered with vehicle (saline) were subject to the same protocol (control). Results are showed as average and average standard deviation SEM, n=5.

The results indicate that the inguinal adipose tissue mass was smaller in animals that received Pep 19 in comparison with the groups that received Rimonabant and/or saline.

Example 10

Test in Brown Adipose Tissue

Figure 18:
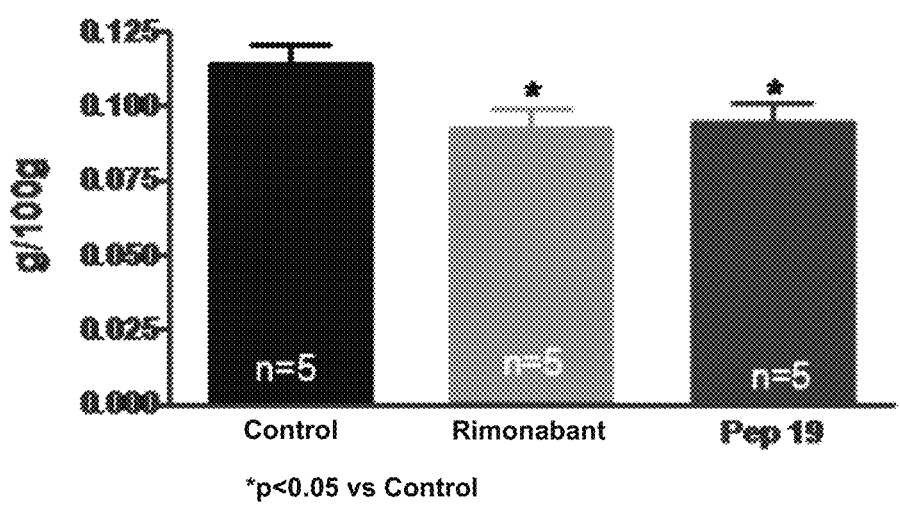
FIG. 18 shows the experimental results in brown adipose tissue for a preferred peptide concretization of the present invention (SeqID:1) and comparison to the control and to the Rimonabant.

FIG. 18 shows the application effects of a preferred peptide concretization of the present invention (SeqID:1 or Pep 19) in a brown adipose tissue model where Thin wistar rats were treated with uma Rimonabant dosage (100 ug/Kg) or peptide 19 (Pep 19 100 ug/Kg) during 3 days orally. The measure of the adipose tissue was performed after finishing the treatment. The results are expressed by the brown adipose tissue weight measured at the treatment end (scale of g/100 g). Rats administered with vehicle (saline) were subject to the same protocol (control). Results are showed as average and average standard deviation SEM, n=5.

The results indicate that the brown adipose tissue mass was smaller in animals that received Pep 19 in comparison with the groups that received Rimonabant and/or saline.

Example 11

Test in Mesenteric Adipose Tissue

Figure 19:
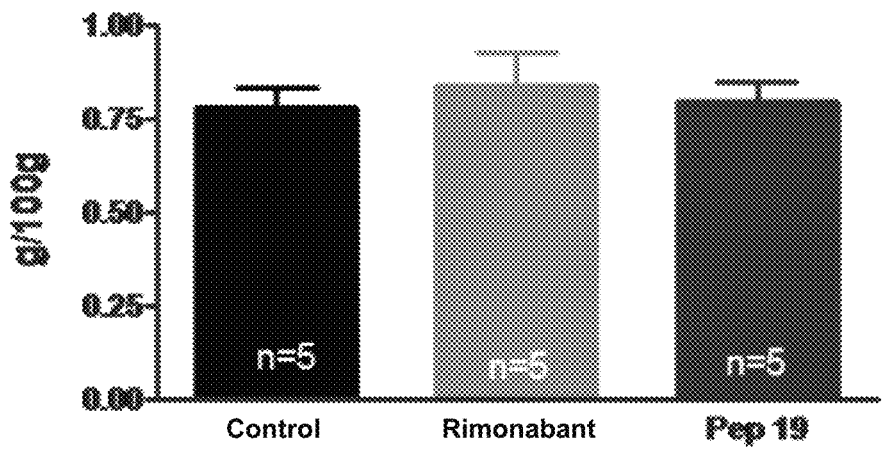
FIG. 19 shows the experimental results in mesenteric adipose tissue for a preferred peptide concretization of the present invention (SeqID:1) and comparison to the control and to the Rimonabant.

FIG. 19 shows the application effects of a preferred peptide concretization of the present invention (SeqID:1 or Pep 19) in a mesenteric adipose tissue model where Thin wistar rats were treated with a Rimonabant dosage (100 ug/Kg) or peptide 19 (Pep 19 100 ug/Kg) during 3 days orally. The measure of the adipose tissue was performed after finishing the treatment. The results are expressed by the mesenteric adipose tissue weight measured at the treatment end (scale of g/100 g). Rats administered with vehicle (saline) were subject to the same protocol (control). Results are showed as average and average standard deviation SEM, n=5.

The results indicate that there is no difference nain the mesenteric adipose tissue mass between the animals that received Pep 19 in comparison with the groups that received Rimonabant and/or saline.

Example 12

Adiposity Ratio Determination

Figure 20:
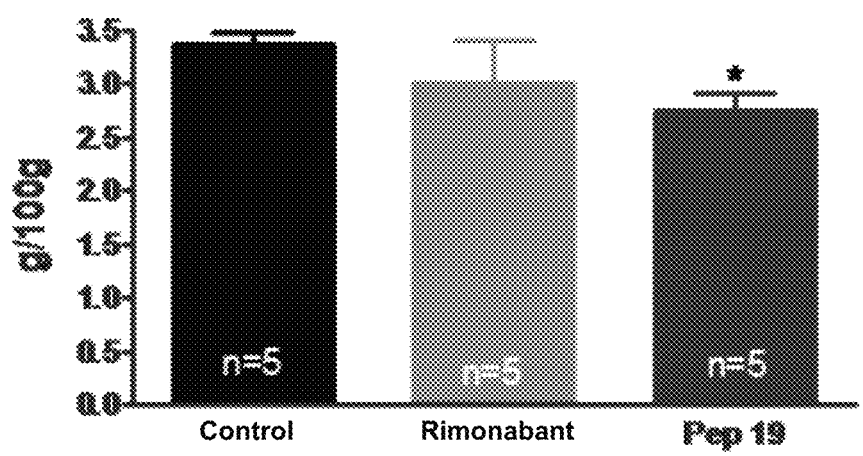
FIG. 20 shows the experimental results related to the adiposity ratio for a preferred peptide concretization of the present invention (SeqID:1) and comparison to the control and to the Rimonabant.

FIG. 20 shows the application effects of a preferred peptide concretization of the present invention (SeqID:1 or Pep 19) over the adiposity ratio in animals. Thin wistar rats were treated with a Rimonabant dosage (100 ug/Kg) or peptide 19 (Pep 19 100 ug/Kg) during 3 days orally. The measure of the adiposity ratio was performed after finishing the treatment using the formula (%), (I=Σ fat deposits/body weight×100). The results are expressed by the animal weight measured at the treatment end (scale of g/100 g). Rats administered with vehicle (saline) were subject to the same protocol (control). Results are showed as average and average standard deviation SEM, n=5.

The results indicate that the adiposity ratio was smaller in animals that received Pep 19 in comparison with the groups that received Rimonabant and/or saline.

Example 13

Serum Leptin Concentration Determination

Figure 21:
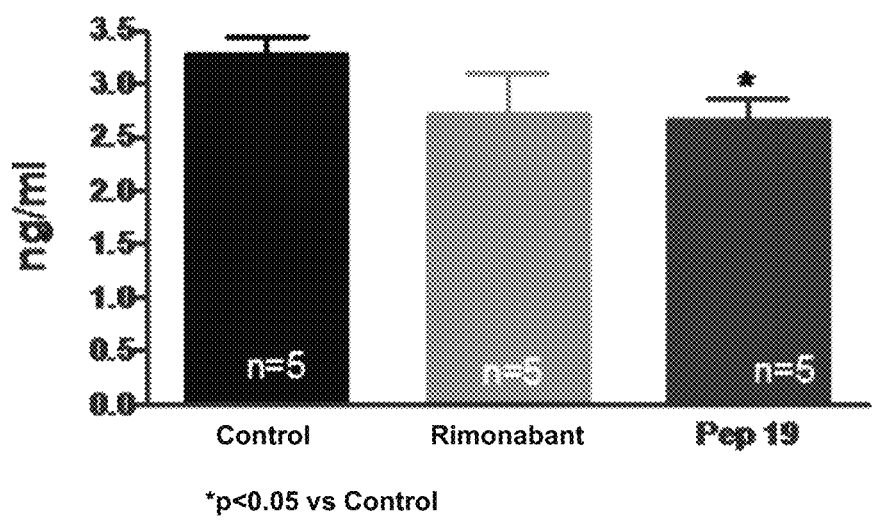
FIG. 21 shows the experimental results about the serum leptin concentration for a preferred peptide concretization of the present invention (SeqID:1) and comparison to the control and to the Rimonabant.

FIG. 21 shows the application effects of a preferred peptide concretization of the present invention (SeqID:1 or Pep 19) over the serum leptin concentration of the animals. Thin wistar rats were treated with a Rimonabant dosage (100 ug/Kg) or peptide 19 (Pep 19 100 ug/Kg) during 3 days orally. The measure of the serum leptin concentration was performed after finishing the treatment. The results are expressed ng/mL. Rats administered with vehicle (saline) were subject to the same protocol (control). Results are showed as average and average standard deviation SEM, n=5.

The results indicate that the serum leptin concentration was smaller in animals that received Pep 19 in comparison with the group that received saline.

Example 14

Determination of CB1 and CB2 Protein Expression in the Brown Adipose Tissue

Figure 22:
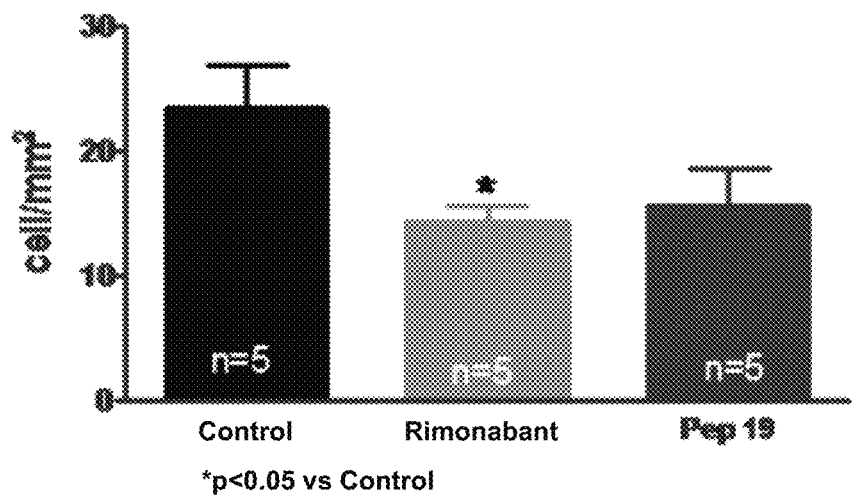
FIG. 22 shows the experimental results about the protein expression of CB1 and CB2 in the brown adipose tissue for a preferred peptide concretization of the present invention (SeqID:1) and comparison to the control and to the Rimonabant.
Figure 22:
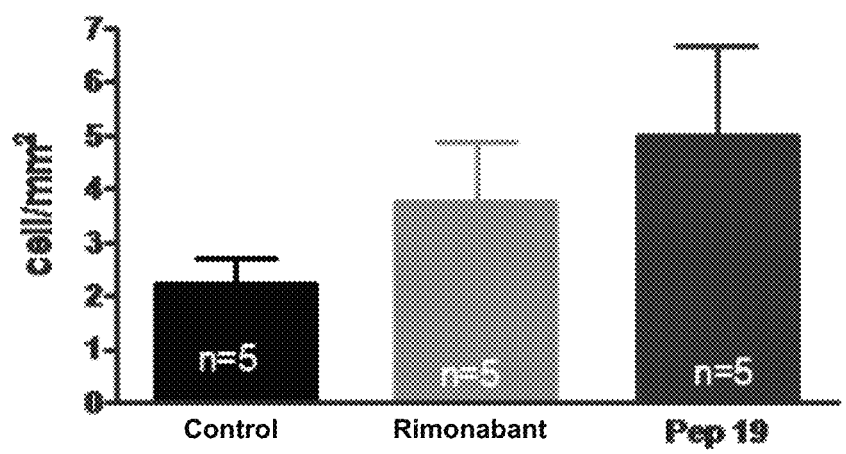

FIG. 22 shows the application effects of a preferred peptide concretization of the present invention (SeqID:1 or Pep 19) over CB1 and CB2 protein expression in the brown adipose tissue of the animals. Thin wistar rats were treated with a Rimonabant dosage (100 ug/Kg) or peptide 19 (Pep 19 100 ug/Kg) during 3 days orally. The measure of the protein expression was performed after finishing the treatment. The results are expressed cell/mm$^2$. Rats administered with vehicle (saline) were subject to the same protocol (control). Results are showed as average and average standard deviation SEM, n=5.

Example 15

Determination of the Weight in Supplemented with 20% Sucrose

Figure 23:
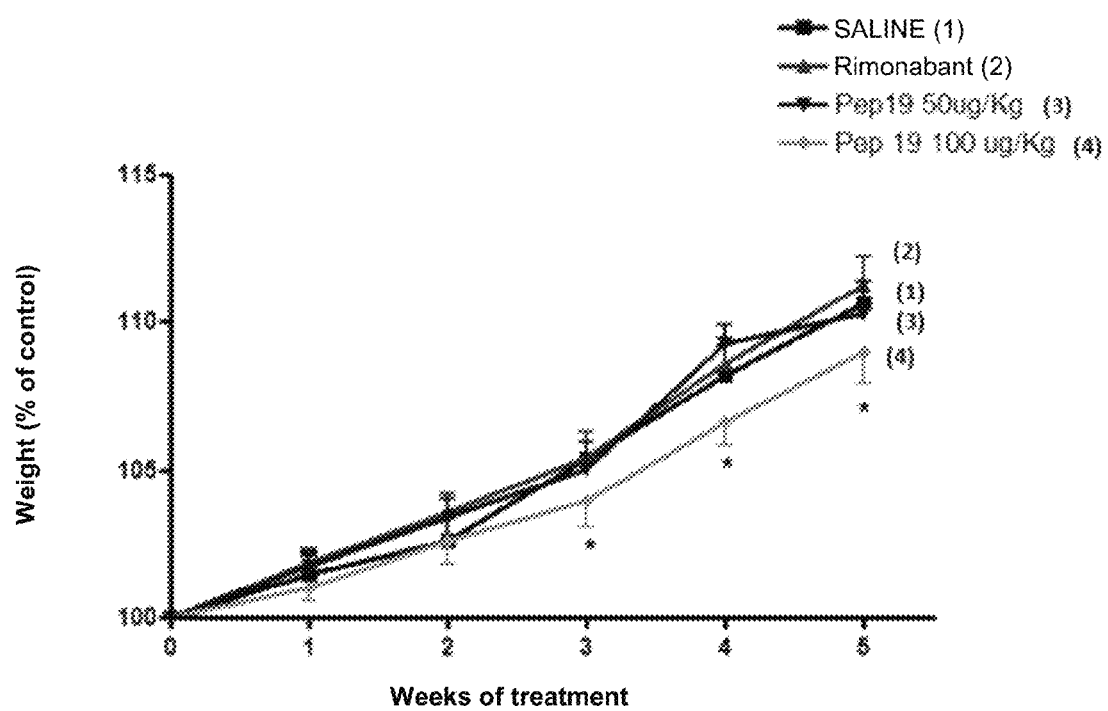
FIG. 23 shows the experimental results regarding the weight in animals supplemented with 20% sucrose for a preferred peptide concretization of the present invention (SeqID:1) and comparison to the control and to the Rimonabant.

FIG. 23 shows the application effects of a preferred peptide concretization of the present invention (SeqID:1 or Pep 19) over the weight in animals supplemented with 20% sucrose. Rats wistar fed with standard regimen supplemented with 20% sucrose were used in the drinking water during 60 days before and during the 30 days-treatment with SALINE (negative control), Rimonabant (positive control), Peptide 19 (Pep 19) in the concentration of 50 μg/Kg and Peptide 19 (Pep 19) in the concentration of 100 μg/Kg. The results were showed in % from the animals weight treated with SALINE (negative control), and analyzed by the Two-way ANOVA test and post-test Bonferroni, n=10.

The results indicate that the animals treated with Peptide 19 in the concentration of 100 μg/Kg showed the lower weight percentages from the 3th to the 5th week of treatment.

Example 16

Determination of the Weight in Animals Supplemented with 20% Sucrose

Figure 24:
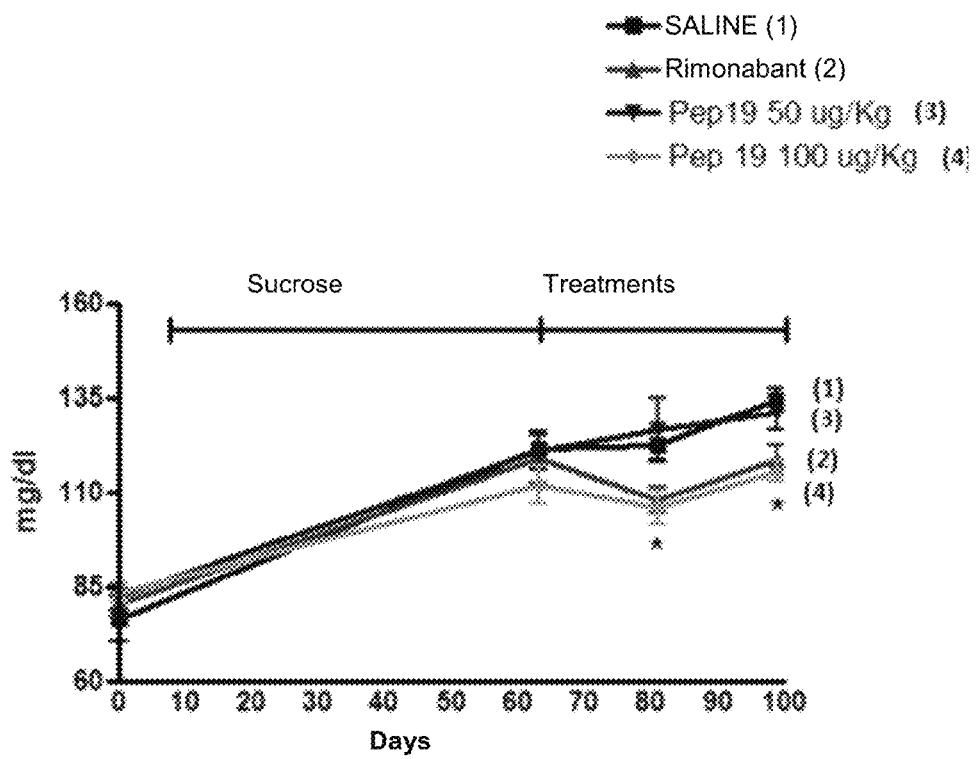
FIG. 24 shows the experimental results regarding the glucose in animals supplemented with 20% sucrose for a preferred peptide concretization of the present invention (SeqID:1) and comparison to the control and to the Rimonabant.

FIG. 24 shows the application effects of a preferred peptide concretization of the present invention (SeqID:1 or Pep 19) over the glucose in animals supplemented with 20% sucrose. Winstar rats fed with standard regimen supplemented with 20% sucrose were used in the drinking water during 60 days before and during the 30 days-treatment with SALINE (negative control), Rimonabant (positive control), Peptide 19 (Pep 19) in the concentration of 50 μg/Kg and Peptide 19 (Pep 19) in the concentration of 100 μg/Kg. Data was collected before and after 60 days of supplementation and in the 15th and 30th days of treatment and were showed in average±SEM and analyzed by the Two-way ANOVA test and post-test Bonferroni, n=10.

The results indicate that the animals treated with the animals treated with Rimonabant (positive control) and Peptide 19 in the concentration of 100 μg/Kg showed the lower glycaemia in the 15th and 30th days of treatment.

Example 17

Determination of the Insulinemia in Animals Supplemented with 20% Sucrose

Figure 25:
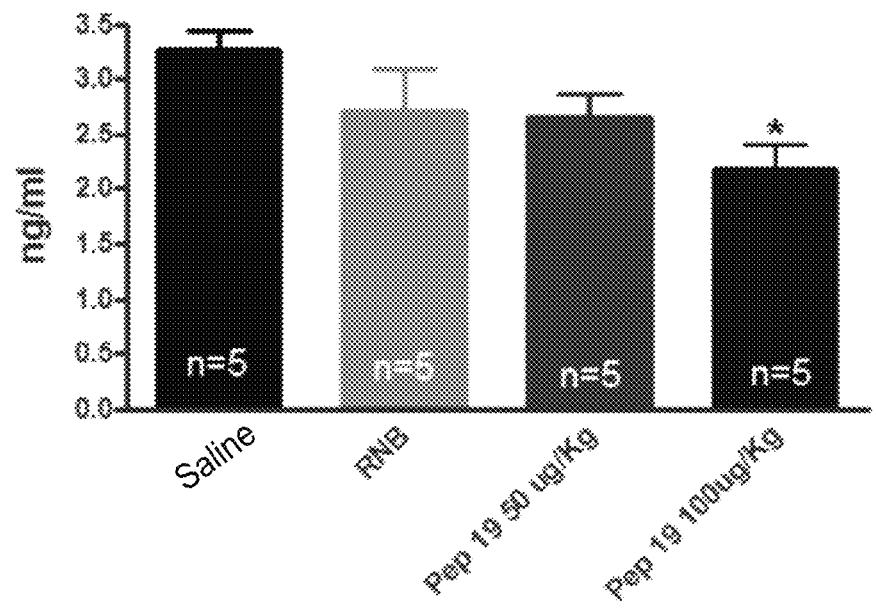
FIG. 25 shows the experimental results regarding the insulinemia in animals supplemented with 20% sucrose for a preferred peptide concretization of the present invention (SeqID:1) and comparison to the control and to the Rimonabant.

FIG. 25 shows the application effects of a preferred peptide concretization of the present invention (SeqID:1 or Pep 19) over the insulinemia in animals supplemented with 20% sucrose. Wistar rats fed with standard regimen supplemented with 20% sucrose were used in the drinking water during 60 days before and during the 30 days-treatment with SALINE (negative control), Rimonabant (positive control), Peptide 19 (Pep 19) in the concentration of 50 μg/Kg and Peptide 19 (Pep 19) in the concentration of 100 μg/Kg. Data was showed in average±SEM and analyzed by the One-way ANOVA test and post-test Bonferroni, n=10.

The results indicate that the animals treated with Peptide 19 in the concentration of 100 μg/Kg showed the lower average of insulinemia after 30 days-treatment.

Example 18

Determination of the Cholesterol in Animals Supplemented with 20% Sucrose

Figure 26:
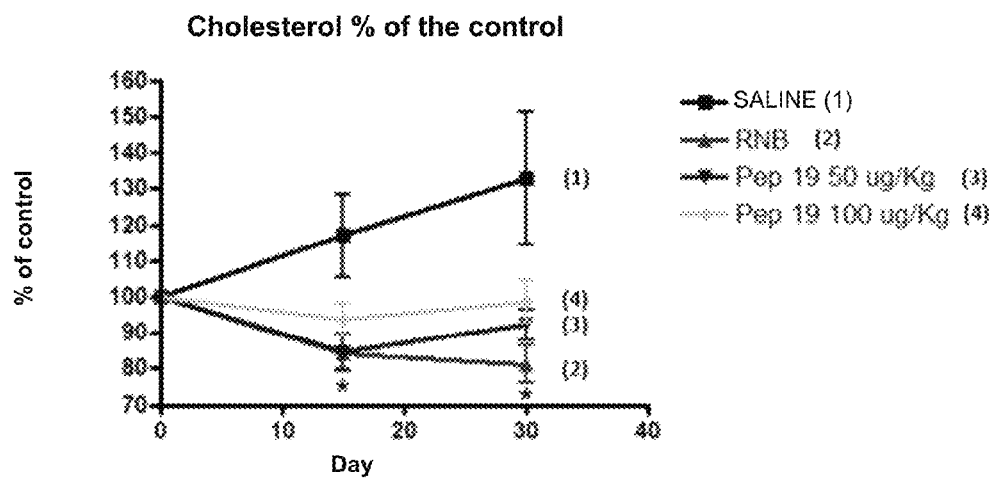
FIG. 26 shows the experimental results regarding the cholesterol levels in animals supplemented with 20% sucrose for a preferred peptide concretization of the present invention (SeqID:1) and comparison to the control and to the Rimonabant.

FIG. 26 shows the application effects of a preferred peptide concretization of the present invention (SeqID:1 or Pep 19) over the cholesterol in animals levels supplemented with 20% sucrose. Wistar rats fed with standard regimen supplemented with 20% sucrose were used in the drinking water during 60 days before and during the 30 days-treatment with SALINE (negative control), Rimonabant (positive control), Peptide 19 (Pep 19) in the concentration of 50 µg/Kg and Peptide 19 (Pep 19) in the concentration of 100 µg/Kg. The results were collected before and after 15th and 30th days of treatment and showed in % from the cholesterol in animals treated with SALINE (negative control), analyzed by the Two-way ANOVA test and post-test Bonferroni, n=10.

The results indicate that the animals treated with Rimonabant (positive control), Peptide 19 in the concentrations of 100 and 50 µg/Kg showed the lower cholesterol percentages after 30 days-treatment.

Example 19

Determination of Triglycerides in Animals Supplemented with 20% Sucrose

Figure 27:
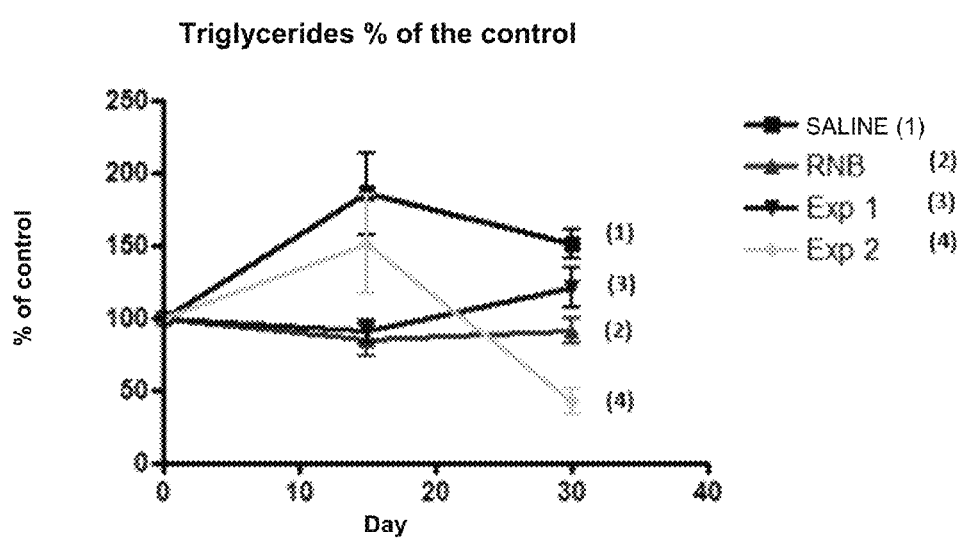
FIG. 27 shows the experimental results regarding the triglycerides levels in animals supplemented with 20% sucrose for a preferred peptide concretization of the present invention (SeqID:1) and comparison to the control and to the Rimonabant.

FIG. 27 shows the application effects of a preferred peptide concretization of the present invention (SeqID:1 or Pep 19) over the triglycerides levels in animals supplemented with 20% sucrose. Wistar rats fed with standard regimen supplemented with 20% sucrose were used in the drinking water during 60 days before and during the 30 days-treatment with SALINE (negative control), Rimonabant (positive control), Peptide 19 (Pep 19) in the concentration of 50 µg/Kg and Peptide 19 (Pep 19) in the concentration of 100 µg/Kg. The results were collected before and after the 15th and 30th days of treatment and showed in % from the triglycerides in animals treated with SALINE (negative control), analyzed by the Two-way ANOVA test and post-test Bonferroni, n=10.

The results indicate that the animals treated with Peptide 19 in the concentration of 100 µg/Kg showed the lower percentages of triglycerides after 30 days-treatment.

Example 20

Figure 28:
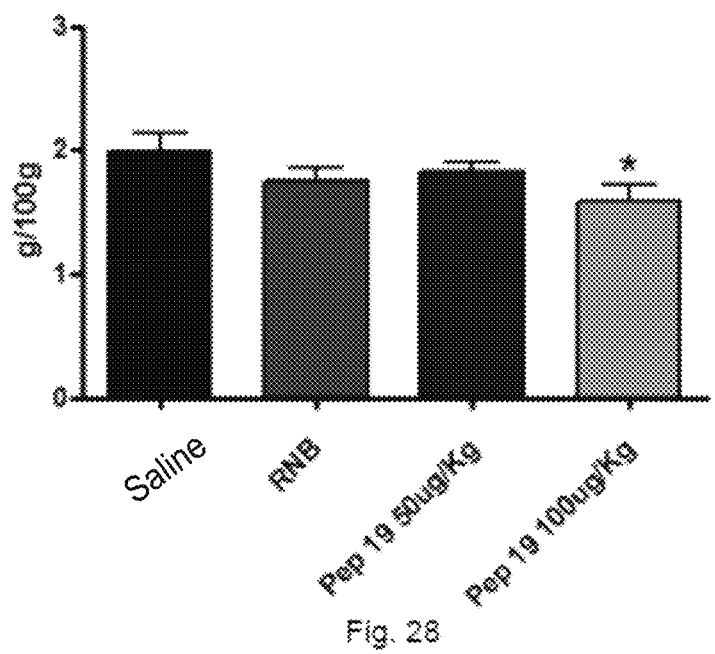
FIG. 28 shows the experimental results regarding the amount of gonadal adipose tissue in animals supplemented with 20% sucrose for a preferred peptide concretization of the present invention (SeqID:1) and comparison to the control and to the Rimonabant.

Determination of the Amount of Gonadal Adipose Tissue in Animals Supplemented with 20% Sucrose FIG. 28 shows the application effects of a preferred peptide concretization of the present invention (SeqID:1 or Pep 19) over the amount of gonadal adipose tissue in animals supplemented with 20% sucrose. Wistar rats fed with standard regimen supplemented with 20% sucrose were used in the drinking water during 60 days before and during the 30 days-treatment with SALINE (negative control), Rimonabant (positive control), Peptide 19 (Pep 19) in the concentration of 50 µg/Kg and Peptide 19 (Pep 19) in the concentration of 100 µg/Kg. The results were collected after the 30th day of treatment and corrected by the body weight of each animal, showed in average±SEM and analyzed by the One-way ANOVA test and post-test Bonferroni, n=10.

The results indicate that the animals treated with Peptide 19 in the concentration of 100 µg/Kg showed the lower percentages of gonadal adipose tissue in comparison to further groups.

Example 21

Figure 29:
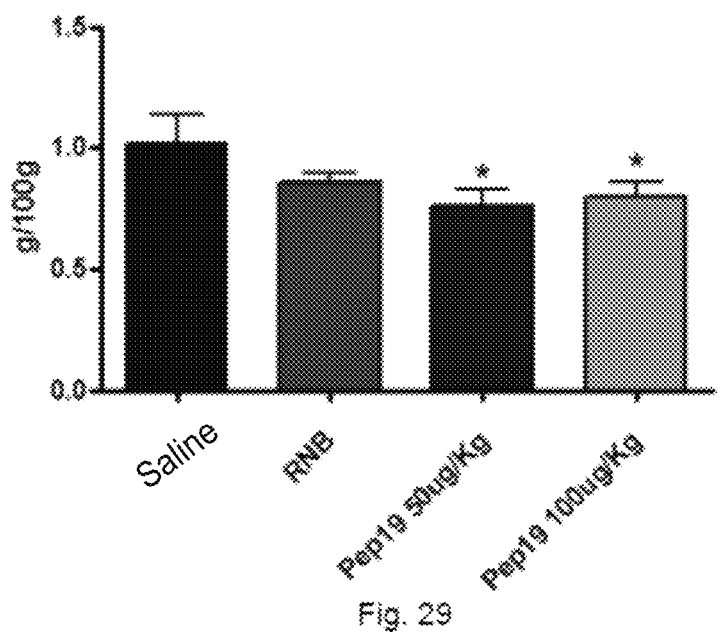
FIG. 29 shows the experimental results regarding the amount of mesenteric adipose tissue in animals supplemented with 20% sucrose for a preferred peptide concretization of the present invention (SeqID:1) and comparison to the control and to the Rimonabant.

Determination of the Amount of Mesenteric Adipose Tissue in Animals Supplemented with 20% Sucrose FIG. 29 shows the application effects of a preferred peptide concretization of the present invention (SeqID:1 or Pep 19) over the amount of mesenteric adipose tissue in animals supplemented with 20% sucrose. Wistar rats fed with standard regimen supplemented with 20% sucrose were used in the drinking water during 60 days before and during the 30 days-treatment with SALINE (negative control), Rimonabant (positive control), Peptide 19 (Pep 19) in the concentration of 50 µg/Kg and Peptide 19 (Pep 19) in the concentration of 100 µg/Kg. The results were collected after the 30th day of treatment and corrected by the body weight of each animal, showed in average±SEM and analyzed by the One-way ANOVA test and post-test Bonferroni, n=10.

The results indicate that the animals treated with Peptide 19 in the concentrations of 50 and 100 µg/Kg showed the lower percentages of mesenteric adipose tissue in comparison to further groups.

Example 22

Figure 30:
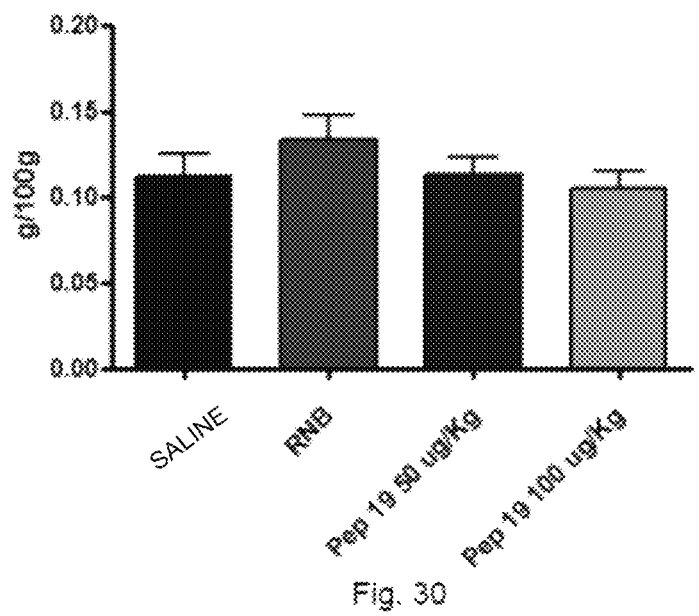
FIG. 30 shows the experimental results regarding the amount of brown adipose tissue in animals supplemented with 20% sucrose for a preferred peptide concretization of the present invention (SeqID:1) and comparison to the control and to the Rimonabant.

Determination of the Amount of Brown Adipose Tissue in Animals Supplemented with 20% Sucrose FIG. 30 shows the application effects of a preferred peptide concretization of the present invention (SeqID:1 or Pep 19) over the amount of brown adipose tissue in animals supplemented with 20% sucrose. Wistar rats fed with standard regimen supplemented with 20% sucrose were used in the drinking water during 60 days before and during o 30 days-treatment with SALINE (negative control), Rimonabant (positive control), Peptide 19 (Pep 19) in the concentration of 50 µg/Kg and Peptide 19 (Pep 19) in the concentration of 100 µg/Kg. The results were collected after the 30th day of treatment and corrected by the body weight of each animal, showed in average±SEM and analyzed by the One-way ANOVA test and post-test Bonferroni, n=10.

Example 23

Figure 31:
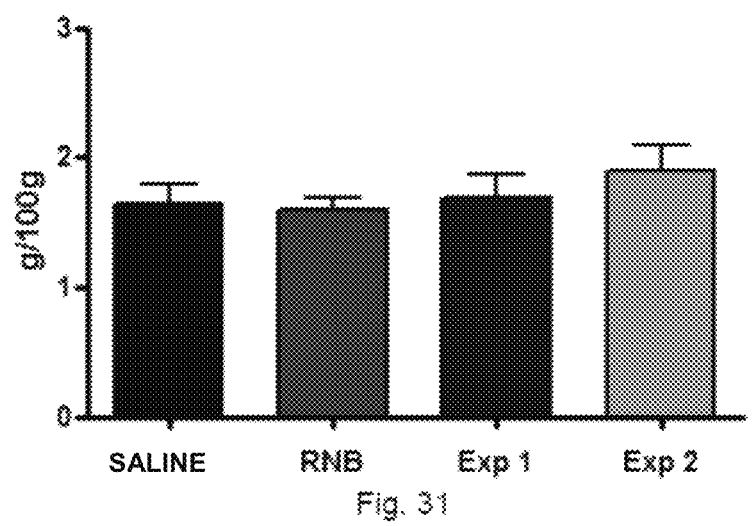
FIG. 31 shows the experimental results regarding the amount of retroperitoneal adipose tissue in animals supplemented with 20% sucrose for a preferred peptide concretization of the present invention (SeqID:1) and comparison to the control and to the Rimonabant.

Determination of the Amount of Retroperitoneal Adipose Tissue in Animals Supplemented with 20% Sucrose FIG. 31 shows the application effects of a preferred peptide concretization of the present invention (SeqID:1 or Pep 19) over the amount of retroperitoneal adipose tissue in animals supplemented with 20% sucrose. Wistar rats fed with standard regimen supplemented with 20% sucrose were used in the drinking water during 60 days before and during the 30 days-treatment with SALINE (negative control), Rimonabant (positive control), Peptide 19 (Pep 19) in the concentration of 50 µg/Kg and Peptide 19 (Pep 19) in the concentration of 100 µg/Kg. The results were collected after the 30th day of treatment and corrected by the body weight of each animal, showed in average±SEM and analyzed by the One-way ANOVA test and post-test Bonferroni, n=10.

Example 24

Figure 32:
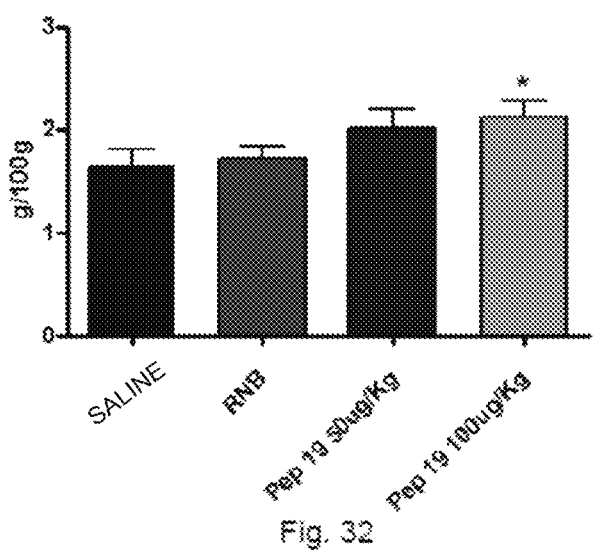
FIG. 32 shows the experimental results regarding the amount of inguinal adipose tissue in animals supplemented with 20% sucrose for a preferred peptide concretization of the present invention (SeqID:1) and comparison to the control and to the Rimonabant.

Determination of the Amount of Inguinal Adipose Tissue in Animals Supplemented with 20% Sucrose FIG. 32 shows the application effects of a preferred peptide concretization of the present invention (SeqID:1 or Pep 19) over the amount of inguinal adipose tissue in animals supplemented with 20% sucrose. Wistar rats fed with standard regimen supplemented with 20% sucrose were used in the drinking water during 60 days before and during the 30 days-treatment with SALINE (negative control), Rimonabant (positive control), Peptide 19 (Pep 19) in the concentration of 50 µg/Kg and Peptide 19 (Pep 19) in the concentration of 100 µg/Kg. The results were collected after the 30th day of treatment and corrected by the body weight of each animal, showed in average±SEM and analyzed by the One-way ANOVA test and post-test Bonferroni, n=10.

The results indicate that the animals treated with Peptide 19 in the concentration of 100 µg/Kg showed the biggest amounts of inguinal adipose tissue in comparison to further groups.

Example 25

Determination of the Adiposity Ratio in Animals Supplemented with 20% Sucrose

Figure 33:
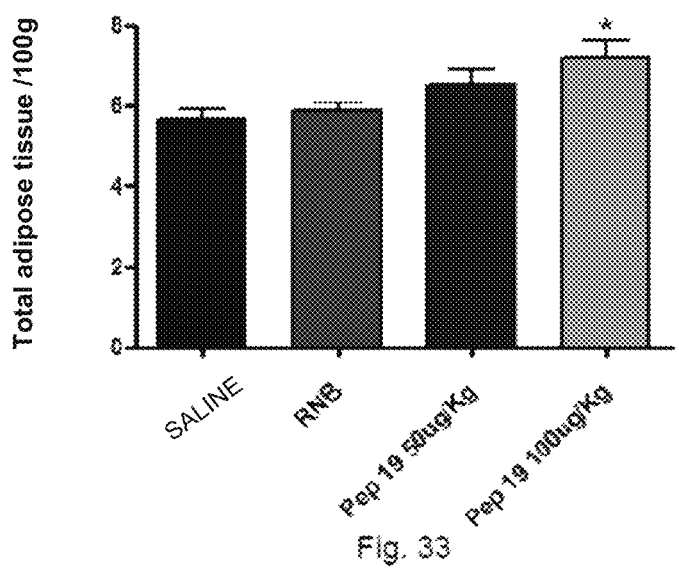
FIG. 33 shows the experimental results regarding the adiposity ratio in animals supplemented with 20% sucrose for a preferred peptide concretization of the present invention (SeqID:1) and comparison to the control and to the Rimonabant.

FIG. 33 shows the application effects of a preferred peptide concretization of the present invention (SeqID:1 or Pep 19) over the adiposity ratio in animals supplemented with 20% sucrose. Wistar rats fed with standard regimen supplemented with 20% sucrose were used in the drinking water during 60 days before and during the 30 days-treatment with SALINE (negative control), Rimonabant (positive control), Peptide 19 (Pep 19) in the concentration of 50 µg/Kg and Peptide 19 (Pep 19) in the concentration of 100 µg/Kg. The adipose tissue total mass was corrected by the body weight of each animal, showed in average±SEM and analyzed by the One-way ANOVA test and post-test Bonferroni, n=10.

The results indicate that the animals treated with Peptide 19 in the concentration of 100 µg/Kg showed the biggest amounts of adipose tissue in comparison to further groups.

Example 26

Determination of the Adiposity Ratio in Animals Supplemented with 20% Sucrose

Figure 34:
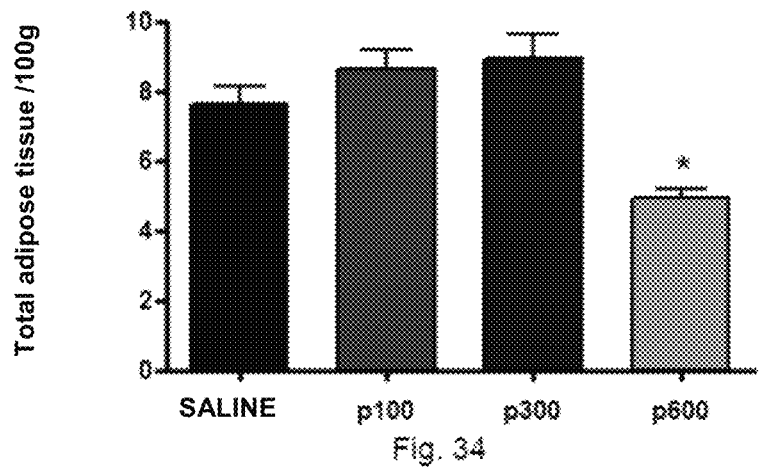
FIG. 34 shows the experimental results regarding the adiposity ratio in animals supplemented with 20% sucrose for a preferred peptide concretization of the present invention (SeqID:1) and comparison to the control and to the Rimonabant.

FIG. 34 shows the application effects of a preferred peptide concretization of the present invention (SeqID:1 or Pep 19) over the adiposity ratio in animals supplemented with 20% sucrose. Wistar rats fed with standard regimen supplemented with 20% sucrose were used in the drinking water during 60 days before and during the 30 days-treatment with SALINE (negative control), Rimonabant (positive control), Peptide 19 (Pep 19) in the concentration of 100 µg/Kg, 300 µg/Kg and 600 µg/Kg. The adipose tissue total mass was corrected by the body weight of each animal, showed in average±SEM and analyzed by the One-way ANOVA test and post-test Bonferroni, n=10.

The results indicate that the animals treated with Peptide 19 in the concentration of 600 µg/Kg showed the lower amounts of adipose tissue in comparison to further groups.

Example 27

Determination of the Blood Pressure in Animals Supplemented with 20% Sucrose

Figure 35:
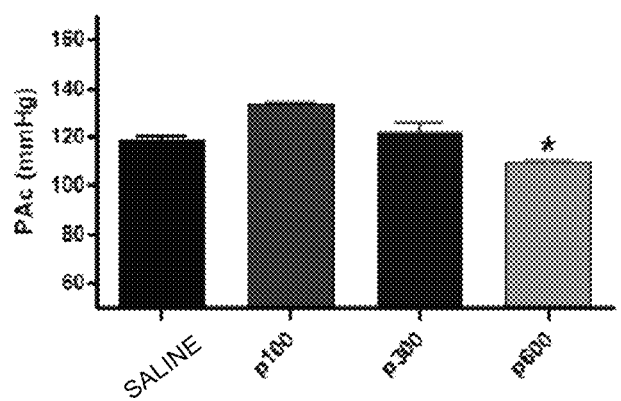
FIG. 35 shows the experimental results regarding the blood pressure in animals supplemented with 20% sucrose for a preferred peptide concretization of the present invention (SeqID:1) and comparison to the control and to the Rimonabant.

FIG. 35 shows the application effects of a preferred peptide concretization of the present invention (SeqID:1 or Pep 19) over the blood pressure in animals supplemented with 20% sucrose. Wistar rats fed with standard regimen supplemented with 20% sucrose were used in the drinking water during 60 days before and during the 30 days-treatment with SALINE (negative control), Rimonabant (positive control), Peptide 19 (Pep 19) in the concentration of 100 µg/Kg, 300 µg/Kg and 600 µg/Kg. The adipose tissue total mass was corrected by the body weight of each animal, showed in average±SEM and analyzed by the One-way ANOVA test and post-test Bonferroni, n=10.

The results indicate that the animals treated with Peptide 19 in the concentration of 600 µg/Kg showed the lower blood pressure in comparison to further groups.

Those skilled in the art will immediately appreciate the teachings here disclosed and will know, from the examples of concretization taught, to reproduce it in other embodiment, and must be considered inside the scope of the invention and attached claims.

The invention claimed is:

1. A modified non-natural peptide comprising the sequence $AA_1$-Asp-$AA_2$-$AA_2$-Ala-Asp-Asp-$AA_3$-$AA_4$, wherein:
   $AA_1$ is an N-terminal tail having between 0-10 amino acids;
   $AA_2$ is a hydrophobic amino acid independently selected from the group consisting of: isoleucine, leucine, phenylalanine, valine, proline, and glycine;
   $AA_3$ is a charged amino acid selected from the group consisting of: arginine, lysine, and glutamic acid; and
   $AA_4$ is a C-terminal tail having between 0-13 amino acids.

2. The modified non-natural peptide according to claim 1, wherein the amino acid tail $AA_1$ is a functionalized tail, wherein the functionalized tail is a TAT tail with 10 amino acids.

3. The modified non-natural peptide according to claim 1, wherein the amino acid tail $AA_4$ has 0 amino acid or the amino acid tail $AA_4$ comprises a sequence having an amino acid selected from the group consisting of proline, leucine, and threonine and combinations thereof.

4. The modified non-natural peptide according to claim 1, wherein the sequence is selected from the group consisting of: SeqID:1; SeqID:2; SeqID:3; SeqID:4; SeqID:5; SeqID:6; their cyclic forms; and combinations thereof.

5. A CB receptor-ligand having at least one non-natural peptide comprising the peptide $AA_1$-Asp-$AA_2$-$AA_2$-Ala-Asp-Asp-$AA_3$-$AA_4$, wherein:
   $AA_1$ is an N-terminal tail having between 0-10 amino acids;
   $AA_2$ is a hydrophobic amino acid independently selected from the group consisting of: isoleucine, leucine, phenylalanine, valine, proline, and glycine;
   $AA_3$ is a charged amino acid selected from the group consisting of: arginine, lysine, and glutamic acid; and
   $AA_4$ is a C-terminal tail having between 0-13 amino acids.

6. The ligand according to claim 5, wherein the ligand is agonist, antagonist, or CB inverse agonist.

7. The ligand according to claim 5, wherein the ligand is selected from the group consisting of: SeqID:1, SeqID:2, SeqID:3, SeqID:4, SeqID:5, their cyclic forms, and combinations thereof.

8. A kit for evaluating the binding to CB receptors, comprising at least one non-natural peptide comprising the peptide $AA_1$-Asp-$AA_2$-$AA_2$-Ala-Asp-Asp-$AA_3$-$AA_4$, wherein:
  $AA_1$ is an N-terminal tail having between 0-10 amino acids;
  $AA_2$ is a hydrophobic amino acid independently selected from the group consisting of: isoleucine, leucine, phenylalanine, valine, proline, and glycine;
  $AA_3$ is a charged amino acid selected from the group consisting of: arginine, lysine, and glutamic acid; and
  $AA_4$ is a C-terminal tail having between 0-13 amino acids.

9. The kit according to claim 8, wherein the non-natural peptide and/or ligand is chemically modified with one or more chromophores and/or radioactive element(s).

10. The modified non-natural peptide according to claim 1, wherein:
  $AA_1$ is an N-terminal tail having 0 amino acids;
  $AA_2$ is a hydrophobic amino acid independently selected from the group consisting of: isoleucine, leucine, phenylalanine, valine, proline, and glycine;
  $AA_3$ is a charged amino acid selected from the group consisting of: arginine, lysine, and glutamic acid; and
  $AA_4$ is a C-terminal tail having 0 amino acids.

11. The ligand according to claim 7, wherein the sequence is selected from the group consisting of: SeqID:1; SeqID:4; and combinations thereof.

12. A pharmaceutical composition for modulating the CB receptors activity in a mammalian, comprising:
  a) a pharmaceutically acceptable vehicle; and one of
  b1) as active ingredient, at least one non-natural peptide comprising the peptide $AA_1$-Asp-$AA_2$-$AA_2$-Ala-Asp-Asp-$AA_3$-$AA_4$, wherein:
    $AA_1$ is an N-terminal tail having between 0-10 amino acids;
    $AA_2$ is a hydrophobic amino acid independently selected from the group consisting of: isoleucine, leucine, phenylalanine, valine, proline, and glycine;
    $AA_3$ is a charged amino acid selected from the group consisting of: arginine, lysine, and glutamic acid; and
    $AA_4$ is a C-terminal tail having between 0-13 amino acids, and
  b2) pharmaceutically acceptable salts of the peptide of b1).

13. The pharmaceutical composition according to claim 12, wherein the at least one non-natural peptide consists essentially of a peptide with an amino acid sequence selected from the group consisting of: SeqID:1; SeqID:2; SeqID:3; SeqID:4; SeqID:5; SeqID:6; their cyclic forms; and combinations thereof.

14. The pharmaceutical composition according to claim 12, wherein the at least one non-natural peptide consists essentially of a peptide with the amino acid sequence of SeqID:1.

15. The pharmaceutical composition according to claim 12, further comprising other active ingredients.

16. The pharmaceutical composition according to claim 12, presented in the form of tablet, gel, or injectable solution.

17. The pharmaceutical composition according to claim 13, wherein the sequence is selected from the group consisting of: SeqID:1; SeqID:4; and combinations thereof.

18. A modified non-natural peptide consisting of the sequence $AA_1$-Asp-$AA_2$-$AA_2$-Ala-Asp-Asp-$AA_3$-$AA_4$, wherein:
  $AA_1$ is an N-terminal tail having between 0-10 amino acids;
  $AA_2$ is a hydrophobic amino acid independently selected from the group consisting of: isoleucine, leucine, phenylalanine, valine, proline, and glycine;
  $AA_3$ is a charged amino acid selected from the group consisting of: arginine, lysine, and glutamic acid; and
  $AA_4$ is a C-terminal tail having between 0-13 amino acids.

19. The modified non-natural peptide according to claim 18, wherein the amino acid tail $AA_1$ is a functionalized tail, wherein the functionalized tail is a TAT tail with 10 amino acids.

20. The modified non-natural peptide according to claim 18, wherein the amino acid tail $AA_4$ has 0 amino acid or the amino acid tail $AA_4$ comprises a sequence having an amino acid selected from the group consisting of proline, leucine, and threonine and combinations thereof.

21. The modified non-natural peptide according to claim 18, wherein the sequence is selected from the group consisting of: SeqID:1; SeqID:2; SeqID:3; SeqID:4; SeqID:5; SeqID:6; their cyclic forms; and combinations thereof.

22. A CB receptor-ligand having at least one non-natural peptide consisting of the peptide $AA_1$-Asp-$AA_2$-$AA_2$-Ala-Asp-Asp-$AA_3$-$AA_4$, wherein:
  $AA_1$ is an N-terminal tail having between 0-10 amino acids;
  $AA_2$ is a hydrophobic amino acid independently selected from the group consisting of: isoleucine, leucine, phenylalanine, valine, proline, and glycine;
  $AA_3$ is a charged amino acid selected from the group consisting of: arginine, lysine, and glutamic acid; and
  $AA_4$ is a C-terminal tail having between 0-13 amino acids.

23. The ligand according to claim 22, wherein the ligand is agonist, antagonist, or CB inverse agonist.

24. The ligand according to claim 22, where the ligand is selected from the group consisting of: SeqID:1, SeqID:2, SeqID:3, SeqID:4, SeqID:5, their cyclic forms, and combinations thereof.

25. A kit for evaluating the binding to CB receptors, comprising at least one non-natural peptide consisting of the peptide $AA_1$-Asp-$AA_2$-$AA_2$-Ala-Asp-Asp-$AA_3$-$AA_4$, wherein:
  $AA_1$ is an N-terminal tail having between 0-10 amino acids;
  $AA_2$ is a hydrophobic amino acid independently selected from the group consisting of: isoleucine, leucine, phenylalanine, valine, proline, and glycine;
  $AA_3$ is a charged amino acid selected from the group consisting of: arginine, lysine, and glutamic acid; and
  $AA_4$ is a C-terminal tail having between 0-13 amino acids.

26. The kit according to claim 25, wherein the non-natural peptide and/or ligand is chemically modified with one or more chromophores and/or radioactive element(s).

27. The modified non-natural peptide according to claim 18, wherein:
  $AA_1$ is an N-terminal tail having 0 amino acids;
  $AA_2$ is a hydrophobic amino acid independently selected from the group consisting of: isoleucine, leucine, phenylalanine, valine, proline, and glycine;
  $AA_3$ is a charged amino acid selected from the group consisting of: arginine, lysine, and glutamic acid; and
  $AA_4$ is a C-terminal tail having 0 amino acids.

28. The ligand according to claim 24, wherein the sequence is selected from the group consisting of: SeqID:1; SeqID:4; and combinations thereof.

29. A pharmaceutical composition for modulating the CB receptors activity in a mammalian, comprising:
a) a pharmaceutically acceptable vehicle; and
b) as active ingredient, at least one non-natural peptide consisting of the peptide $AA_1$-Asp-$AA_2$-$AA_2$-Ala-Asp-Asp-$AA_3$-$AA_4$, wherein:
$AA_1$ is an N-terminal tail having between 0-10 amino acids;
$AA_2$ is a hydrophobic amino acid independently selected from the group consisting of: isoleucine, leucine, phenylalanine, valine, proline, and glycine;
$AA_3$ is a charged amino acid selected from the group consisting of: arginine, lysine, and glutamic acid; and
$AA_4$ is a C-terminal tail having between 0-13 amino acids, or
c) pharmaceutically acceptable salts of the peptide as defined in b).

30. The pharmaceutical composition according to claim 29, wherein the at least one non-natural peptide consists essentially of a peptide with an amino acid sequence selected from the group consisting of: SeqID:1; SeqID:2; SeqID:3; SeqID:4; SeqID:5; SeqID:6; their cyclic forms; and combinations thereof.

31. The pharmaceutical composition according to claim 29, wherein the at least one non-natural peptide consists essentially of a peptide with the amino acid sequence of SeqID:1.

32. The pharmaceutical composition according to claim 29, further comprising other active ingredients.

33. The pharmaceutical composition according to claim 29, presented in the form of tablet, gel, or injectable solution.

34. The pharmaceutical composition according to claim 30, wherein the sequence is selected from the group consisting of: SeqID:1; SeqID:4; and combinations thereof.

35. The modified non-natural peptide according to claim 21, wherein the sequence is SeqID:1.

* * * * *